US008865216B2

(12) United States Patent
Labhasetwar et al.

(10) Patent No.: US 8,865,216 B2
(45) Date of Patent: Oct. 21, 2014

(54) SURFACE-MODIFIED NANOPARTICLES FOR INTRACELLULAR DELIVERY OF THERAPEUTIC AGENTS AND COMPOSITION FOR MAKING SAME

(75) Inventors: Vinod Labhasetwar, Solon, OH (US); Jaspreet Vasir, Cleveland, OH (US)

(73) Assignees: National Institutes of Health (NIH), Bethesda, MD (US); U.S. Dept. of Health and Human Services (DHHS), Washington, DC (US)

( * ) Notice: Subject to any disclaimer, the term of this patent is extended or adjusted under 35 U.S.C. 154(b) by 960 days.

(21) Appl. No.: 12/184,715

(22) Filed: Aug. 1, 2008

(65) Prior Publication Data

US 2009/0136585 A1 May 28, 2009

Related U.S. Application Data

(60) Provisional application No. 60/953,912, filed on Aug. 3, 2007.

(51) Int. Cl.
*A61K 9/51* (2006.01)

(52) U.S. Cl.
CPC ............. *A61K 9/5153* (2013.01); *A61K 9/5146* (2013.01); *Y10S 977/773* (2013.01); *Y10S 977/906* (2013.01)
USPC ..... 424/489; 424/501; 514/772.4; 514/772.6; 514/773; 977/773; 977/906

(58) Field of Classification Search
None
See application file for complete search history.

(56) References Cited

U.S. PATENT DOCUMENTS

| 6,395,253 | B2 | 5/2002 | Levy et al. | |
|---|---|---|---|---|
| 6,814,980 | B2 | 11/2004 | Levy et al. | |
| 2002/0012652 | A1* | 1/2002 | Levy et al. | 424/85.2 |
| 2004/0157215 | A1* | 8/2004 | McCafferty et al. | 435/5 |
| 2005/0090008 | A1* | 4/2005 | Segura et al. | 435/459 |
| 2006/0035854 | A1 | 2/2006 | Goldstein et al. | |
| 2006/0134209 | A1 | 6/2006 | Labhasetwar et al. | |

FOREIGN PATENT DOCUMENTS

WO 9856348 12/1998

OTHER PUBLICATIONS

S Kumar, NR Choudhury. "New strategies for promoting angiogenesis in biodegradable polymeric tissue engineering scaffolds: A materials science approach." http://www.unisa.edu.au/iwri/futurestudents/phdprojects/newstrategies.asp, accessed Mar. 15, 2010.*
C Cui, SP Schwendeman. "Surface Entrapment of Polylysine in Biodegradable Poly(DL-lactide-co-glycolide) Microparticles." Macromolecules, vol. 34, 2001, pp. 8426-8433.*
V Vijayanthan, T Thomas, TJ Thomas. "DNA Nanoparticles and Development of DNA Delivery Vehicles for Gene Therapy." Biochemistry, vol. 41 No. 48, Dec. 3, 2002, pp. 14085-14094.*
IS Kim, SK Lee, YM Park, YB Lee, SC Shin, KC Lee, IJ Oh. "Physicochemical characterization of poly(l-lactic acid) and poly(d,l-lactide-co-glycolide) nanoparticles with polyethylenimine as gene delivery carrier." International Journal of Pharmaceutics, vol. 298, 2005, pp. 255-262.*
H Murakami, Y Kawashima, T Niwa, T Hino, H Takeuchi, M Kobayashi. "Influence of the degrees of hydrolyzation and polymerization of poly(vinylalcohol) on the preparation and properties of poly(DL-lactide-co-glycolide) nanoparticle." International Journal of Pharmaceutics, vol. 149, 1997, pp. 43-49.*
J. Davda et al., "Sustained Proangiogenic Activity of Vascular Endothelial Growth Factor Following Encapsulation in Nanoparticles", J. Biomed. Nanotechnology, 1: 74-82 (2005).
M. Reddy et al., "Targeted Delivery of SOD Encapsulated Nanoparticles to the Brain Reduced Ischemia/Reperfusion Injury", International Stroke Conference, San Francisco, CA (2007).
B. Mayer et al., "Biosynthesis and action of nitric oxide in mammalian cells", Trends Biochem. Sci, 22: 477-81 (1997).
J. Panyam et al., "Dynamics of Endocytosis and Exocytosis of Poly(D,L-Lactide-co-Glycolide) Nanoparticles in Vascular Smooth Muscle Cells", Pharm. Res., 20(2): 212-220 (2003).
S. Prabha et al., "Critical Determinants in PLGA/PLA Nanoparticle-Mediated Gene Expression", Pharm. Res., 21(2): 354-64 (2004).
M.W. Radomski et al., "An L-arginine/nitric oxide pathway present in human platelets regulates aggregation", Proc. Natl. Acad. Sci. USA, 87: 5193-5197 (1990).
J.J. Rome et al., "Anatomic barriers influence the distribution of in vivo gene transfer into the arterial wall. Modeling with microscopic tracer particles and verification with a recombinant adenoviral vector", Arteriosclerosis, Thrombosis, and Vascular Biology, 14: 148-161 (1994).
S. Sahoo et al., "Residual polyvinyl alcohol associated with poly (D,L-lactide-co-glycolide) nanoparticles affects their physical properties and cellular uptake", J. Control Release, 82: 105-114 (2002).
R. Sarkar et al., "Does Nitric Oxide Regulate Smooth Muscle Cell Proliferation", J. Vasc. Res., 35: 135-142 (1998).
G. Zimmerman et al., "Perspective Series; cell Adhesion in Vascular Biology", J. Clin. Invest., 98(8): 1699-1702 (1996).
J. Panyam et al., "Rapid endo-lysosomal escape of poly(DL-lactide-co-glycolide) nanoparticles: implications for drug and gene delivery", FASEB, 16: 1217-1226 (2002).
C. Song et al., "Arterial uptake of biodegradable nanoparticles for intravascular local drug delivery: Results with an acute dog model", J. Control. Release, 54: 201-211 (1998).
V. Labhasetwar et al., "Arterial Uptake of Biodegradable Nanoparticles: Effects of Surface Modifications", J. Pharm. Sci., 87(10) 1229-1234 (1998).
J. Davda et al., "Characterization of nanoparticle uptake by endothelial cells", Int. J. Pharm., 233: 51-59 (2002).
N. Pyo et al., "Effect of the cell type and cell density on the binding of living cells to a silica particle: An atomic force microscope study", Colloids Surf. B. Biointerfaces, 53: 278-287 (2006).

(Continued)

*Primary Examiner* — Frederick Krass
*Assistant Examiner* — Isaac Shomer
(74) *Attorney, Agent, or Firm* — Patrick J. Hagan; Dann, Dorfman, Herrell and Skillman, P.C.

(57) ABSTRACT

Surface-modified polymeric nanoparticles (NPs), compositions for making them, and their use in drug delivery are disclosed.

5 Claims, 21 Drawing Sheets

(56) References Cited

OTHER PUBLICATIONS

S. Cho et al., "The Number of Secretory Vesicles Remains Unchanged Following Exocytosis", 26(1) 29-33 (2002).

H. You et al., "Atomic force microscopy imaging of living cells: progress, problems and prospects", Methods Cell Sci., 21: 1-17 (1999).

H. McNally et al., "Comparative three-dimensional imaging of living neurons with confocal and atomic force microscopy", J. Neurosci. Methods, 142: 177-184 (2005).

L. Shlyakhtenko et al., "Silatrane-based surface chemistry for immobilization of DNA, protein-DNA complexes and other biological materials", Ultramicroscopy, 97: 279-287 (2003).

M. Desai et al., "The Mechanism of Uptake of Biodegradable Microparticles in Caco-2 Cells is Size Dependent", Pharm. Res., 14(11): 1568-1573 (1997).

F. Ohnesorge et al., "AFM Review Study on Pox Viruses and Living Cells", Biophys. J, 73: 2183-2194 (1997).

C. Putman et al., "Viscoelasticity of Living Cells Allows High Resolution Imaging by Tapping Mode Atomic Force Microscopy", Biophys. J., 67: 1749-1753 (1994).

S. Schneider et al., "Surface dynamics in living acinar cells imaged by atomic force microscopy: Identification of plasma membrane structures involved in exocytosis", Proc. Natl. Acad. Sci. USA, 94: 316-321 (1997).

R.E. Marchant et al., "Molecular Views and Measurements of Hemostatic Processes Using Atomic Force Microscopy", Curr. Protein Pept. Sci., 3: 249-274 (2002).

J. Panyam et al., "Fluorescence and electron microscopy probes for cellular and tissue uptake of poly(D,L-lactide-co-glycolide) nanoparticles", Int. J. Pharm., 262: 1-11 (2003).

S. Schaus et al., "Cell Viability and Probe-Cell Membrane Interactions of XR1 Glial Cells Imaged by Atomic Force Microscopy", Biophys. J., 73: 1205-1214 (1997).

K. Sinniah et al., "Investigating live and fixed epithelial and fibroblast cells by atomic force microscopy", Curr. Eye Res., 25(1): 61-68 (2002).

\* cited by examiner dX:77.51 nm    dY:48.49 nm

FIG. 8a
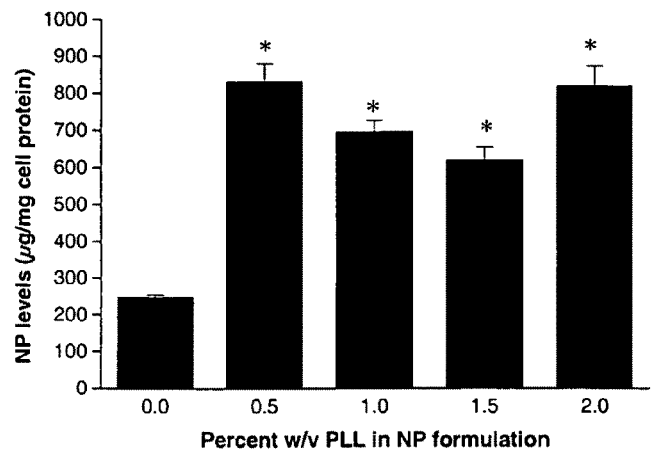
FIG. 8b
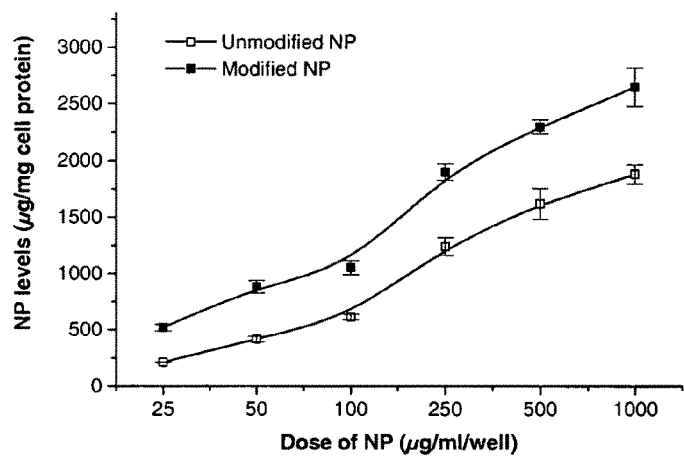
FIG. 8

SURFACE-MODIFIED NANOPARTICLES FOR INTRACELLULAR DELIVERY OF THERAPEUTIC AGENTS AND COMPOSITION FOR MAKING SAME

CROSS-REFERENCE TO RELATED APPLICATIONS

The present application claims the benefit of U.S. Provisional Patent Application No. 60/953,912, filed Aug. 3, 2007, the entire disclosure of which is incorporated by reference herein.

STATEMENT REGARDING FEDERAL SPONSORED RESEARCH OR DEVELOPMENT

This invention was made with government support under Grant No. 1RO1 EB 003975-01A1 awarded by the U.S. National Institutes of Health. The Government has certain rights in this invention.

BACKGROUND

As a result of numerous studies elucidating the mechanism of targeted drug delivery, various drug-carrier systems (including nanoparticle (NP) systems), that incorporate a multifunctional surface are being developed. All such systems are based on the premise that particular ligands can only be recognized by specific cell-types and not by others, thus delivering the drug payload only in the targeted tissue. This interaction of NPs with biological membrane is an important determinant in their cellular internalization, which could depend on various factors such as NP size and surface characteristics (e.g., charge, targeting ligand, etc.), as well as on the cell membrane components. Following cellular uptake, the subcellular sorting of NP into different intracellular compartments and retention could depend on their interaction with the components of endocytic machinery, cytoskeletal components and subcellular organelles. Though functionalization of NPs is increasingly explored, successful development of efficient nanocarriers is hindered by a limited understanding and lack of methodology for assessment of the nanocarrier interaction with cellular components as well as their intracellular trafficking. Consequently, it is imperative to increase understanding of the influence of surface functionalization on the NP-cell interactions and ultimately, the phenomena of cellular internalization of NPs, with a view toward improving targeted cell delivery by minimizing non-specific interactions with non-target cells and increasing the affinity of NPs toward target cells.

NPs used for drug delivery are polymeric colloidal systems (~100 nm diameter) formulated from a FDA-approved biodegradable and biocompatible polymer, e.g. poly DL-lactide-co-glycolide (PLGA), with one or more therapeutic agent of interest loaded in or on the particles. Polymeric NPs can be formulated to incorporate various types of therapeutic agents, including low molecular weight drugs or small molecules and macromolecules such as proteins or plasmid DNA [1,2]. PLGA NPs loaded with therapeutic agents are of special interest for intracellular drug delivery owing to their biocompatibility, biodegradability and ability to sustain therapeutic drug levels for prolonged periods of time. Moreover, the duration and levels of drug released from the NPs can be easily modulated by altering formulation parameters such as drug:polymer ratio, or polymer molecular weight and composition [3].

Various techniques have been reported for preparing polymeric NPs incorporating surface-modifying agents, such as heparin, dodecylmethylammonium bromide (DMAB), DEAE-Dextran, lipofectin, and fibrinogen [4, 5]. These techniques include:

chemical coupling of the modifying agent to the surface of pre-formed NPs;

incorporation of the modifying agent within the polymer matrix of the NP, which involves dissolution of the modifying agent into the polymer solution used to form the NPs;

adsorption of the modifying agent onto the surface of pre-formed NPs.

In the resultant NPs, the modifying agents are either present on the NP surface, due to covalent bonding via chemical coupling agent or physical adsorption, or distributed throughout the polymer matrix. In each case, the modifying agent imparts a cationic charge to the NP surface. In the case of DMAB modification, the surface charge remains cationic, regardless of the pH value of the environment to which the NPs are exposed.

The present inventors previously carried out studies which demonstrated that biodegradable PLGA NPs following cellular internalization (via endocytosis) undergo surface charge reversal (anionic to cationic) in the acidic pH of endo-lysosomes, thus facilitating their escape into the cytosolic compartment [6-8]. However, a significant fraction of NPs undergo exocytosis and only 15% of the internalized NPs escape into the cytosolic compartment. Thus, a rapid reversal of surface charge of NPs from negative to positive is considered to be the key to rapid escape of NPs from the deleterious acidic environment of the endo-lysosomes, into the cytosol. The amount of residual poly vinyl alcohol (PVA) associated with such NPs is believed to be responsible for this surface charge reversal phenomenon and, therefore, surface charge of the NPs could be altered by varying the concentration of PVA used as an emulsifier in the formulation. This belief is based on the observation that NPs with lower amount of surface associated PVA show about 3-fold higher cellular uptake in vascular smooth muscle cells (VSMCs) than the NPs with higher residual PVA [7]. Furthermore, the amount of PVA associated with the NP surface depends on the amount of PVA, the molecular weight and degree of hydroxylation of PVA used as emulsifier in the formulation [3]. Thus, the surface properties of NPs play an important role in their cellular uptake and can potentially influence the efficiency of cytosolic drug delivery.

Having shown that polymeric NPs are capable of endo-lysosomal escape due to their selective surface charge reversal in the acidic environment within endo-lysosomes, further investigation was conducted for alternative NP formulations having improved cellular uptake and more efficient cytoplasmic drug delivery.

SUMMARY OF THE INVENTION

It has been discovered in accordance with the present invention that the surface of polymeric NPs can be modified to increase the force and occurrence of NP interactions with cell membrane, and improve upon the efficiency of intracellular delivery of therapeutic agents. These improved properties make the NPs of the present invention useful for cytoplasmic drug delivery.

According to one aspect of the present invention, there is provided a composition for producing modified NPs suitable for drug delivery which comprises a biocompatible polymer having a net negative surface charge in formed NPs (i.e., NPs formed from such polymer) at neutral pH, at least one charge modulator that is effective to reverse the surface charge from negative to positive in an acidic environment and, optionally, an amphiphilic emulsifier.

The present invention further provides a modified NP for delivery of therapeutic agents which is made from the above-described composition, and which exhibits greater force of adhesion to a cell membrane, as compared to an unmodified NP, and improved efficiency of intracellular delivery of therapeutic agents carried by such NP.

There is also provided in accordance with this invention a method for making the above-described surface-modified NPs. This method involves: (i) forming a primary water-in-oil emulsion comprising an aqueous solution of a bioactive agent and a solution of a biocompatible polymer in an organic solvent, the polymer having a net negative surface charge in formed NPs at neutral pH, (ii) mixing the primary water-in-oil emulsion with an aqueous solution of a charge modulator, and optionally, an amphiphilic emulsifier to form a multiple water-in-oil-in-water emulsion, (iii) removing the organic solvent and (iv) recovering the surface-modified NPs.

NPs produced by this method have the charge modulator disposed on the surface thereof. In the case of the charge modulator poly-L-lysine (PLL), for example, the backbone of the molecule is embedded into the polymeric matrix and the hydrophilic side chains extend outwardly from the NP surface. Consequently, the functional groups of the PLL are available at the interface. This allows for modulating the surface properties of the NPs in response to changes in outside conditions, such as pH, and for cell membrane interactions. By contrast, where a modifying agent is incorporated into the polymer matrix, the functional groups thereof will not be available at the interface. In the case of adsorption of a modifying agent onto pre-formed NPs, the availability of its functional groups is effectively masked by the coating agent used. NPs of the present invention are also distinguishable from prior art NPs in which the modifying agent is bound to the NPs via ionic interaction or covalent bonds.

The NPs of the present invention can be loaded with a variety of bioactive agents, as will appear in the following detailed description.

Insofar as is known, surface-modified NPs formulated as described herein, which are characterized by the ability to reverse the surface charge thereof from negative to positive in an acidic environment, while maintaining a high force of interaction with the cell surface, and a composition and method for the preparation of such NPs have not previously been described.

BRIEF DESCRIPTION OF THE DRAWINGS

FIG. 6a is an uncoated AFM tip; FIG. 6b is an AFM tip placed in NP formulation, after which organic solvent is evaporated under vacuum. FIG. 6c—the AFM tip is washed with water and dried in Argon gas. FIG. 6d is an AFM tip coated with NPs. FIG. 6e is an AFM image of NPs prepared on the surface of freshly cleaved mica.

FIG. 8a is a graphical representation of cellular uptake of NPs prepared with different amounts of PLL and PVA in the formulation; FIG. 8b is a graphical representation showing the dose dependence of uptake of NPs in MDA-MB435S cells incubated with different doses of unmodified and modified NPs, which was quantitatively determined using HPLC. Amount of NPs analyzed by HPLC was normalized to the total cell protein. Data is presented as mean±SEM, n==6. (*) p<0.05.

DETAILED DESCRIPTION OF THE INVENTION

Figure 1A:
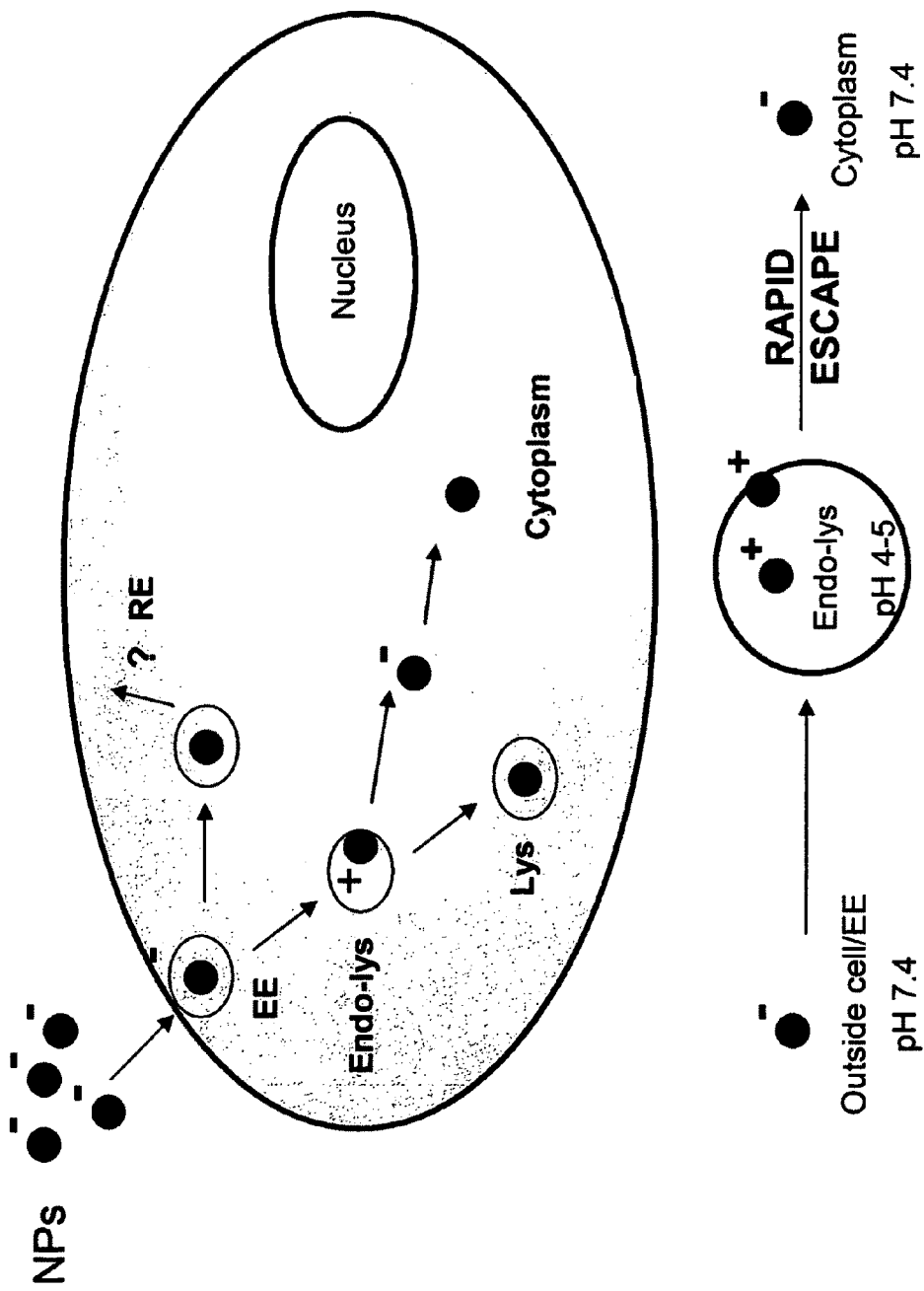
FIG. 1a is a schematic depicting the cellular uptake and endosomal escape of NPs.

PLGA-NPs with entrapped therapeutic agents are preferred for intracellular drug delivery owing to their biocompatibility, biodegradability and ability to sustain therapeutic drug levels for prolonged periods of time. The polymeric matrix prevents the degradation of the entrapped drug, and also allows precise control over the release kinetics of the drug from NPs. Polymeric NPs, formed from PLGA exhibit a negatively charged surface at neutral pH, owing to the presence of uncapped carboxylic acid end groups on the polymer. Based on the above-mentioned studies [6-8], it was hypothesized that the mechanism responsible for the observed rapid endo-lysosomal escape of polymeric NPs is selective surface charge reversal of NPs from anionic to cationic in the acidic pH of the endo-lysosomal compartment which facilitates the escape into the cytosolic compartment, thereby enhancing the efficiency of intracellular drug delivery (FIG. 1a). To test this hypothesis, surface modified NPs embodying the present invention were formulated, using different combinations of PVA (emulsifier) and PLL, a well known gene transfection agent, which is used as a charge modulator in the formulation of the invention. PVA and PLL, being amphiphilic, anchor on the PLGA polymer via their hydrophobic ends, and thus shield the negative charge of the carboxylic end groups of the polymer. The hydroxyl and amino groups of PVA and PLL respectively, can be protonated at acidic pH, thus contributing a positive charge to the NP surface. By titrating the concentrations of PVA and PLL (i.e., the surface hydroxyl and amino groups) in the NPs, a rapid reversal of surface charge from negative to positive can be achieved in the acidic environment of endo-lysosomes.

Figure 1B:
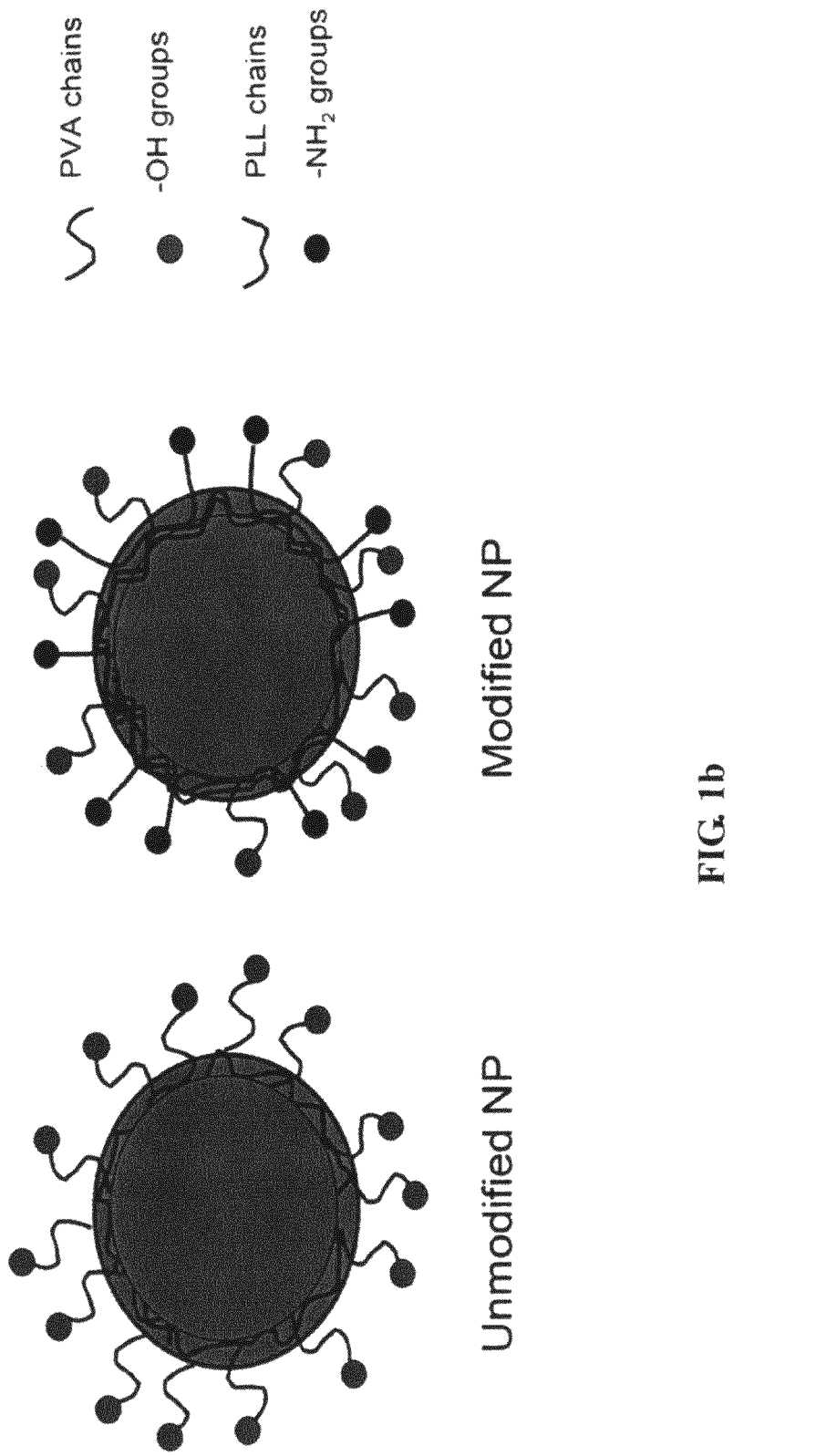
FIG. 1b is a schematic depicting the surface modification of NPs.

NPs formulated with PVA alone are referred to herein as unmodified NPs, whereas those prepared using the combination of PVA (or other amphiphilic emulsifier) with PLL (or other charge modulator) are referred to herein as modified or surface modified NPs (FIG. 1b). Generally speaking, surface modification of NPs in accordance with this invention produces a significant increase in the cellular uptake, as compared to unmodified NPs.

Although not wishing to be bound to any particular theoretical basis for the observed NP behavior, the PVA, or other amphiphilic emulsifier, is believed to provide steric stability to NPs to prevent their aggregation, and PLL at the interface is believed to modulate the surface charge in an acidic pH range.

As described in further detail below, cellular interactions and the dynamics of intracellular trafficking of NPs were studied in MDA-MB-435S breast cancer cells. Atomic force microscopy (AFM) was used for time-lapse imaging of live cell membrane following incubation with the NPs of the invention, and to measure the force of interaction of NPs with cell membrane. Fluorescently labeled PLGA-NPs were used with different fluorescent markers for sub-cellular compartments to study the trafficking and sorting of NPs following their cellular uptake. These studies demonstrate that the force of NP-cell interaction determines the affinity of NPs for cells, and likewise determines the extent of cellular uptake of NPs.

Although the present invention is described hereinbelow with reference to NPs composed of PLGA, PLL and PVA, as the presently preferred embodiment of the invention, it should be understood that NPs having comparable properties to those of the preferred embodiment can be made using other materials. In addition to PLGA, other biocompatible polymers include, without limitation, polylactides, polyglycolides, polyanhydrides, polyorthoesters, polycyanoacrylates, polycaprolactone, poly(alkylene glycol), poly (methylmethacrylate), poly(methylacrylic acid), poly (methylmethacrylate-co-methacrylic acid), polyallylamine and polyhydroxybutyric acid. Polymer molecular weight is preferably in the range of 10,000 to several hundreds of thousands, and in particular, from 20,000-140,000.

Suitable charge modulators which may be used in carrying out the invention include, without limitation, cationic proteins, e.g. histones and protamines, or synthetic cationic polymers, e.g. polylysine, polyarginine, polyornithine, DEAE-Dextran, polybrene, polyethylenimine, or the like. Charge modulators may be used in combination in the practice of this invention.

Any biocompatible amphiphilic emulsifier may be used as the emulsifier in the composition of the invention. Suitable amphiphilic emulsifiers include, without limitation, PVA, PEG (MW of 6,000-20,000) derivatives of PEG, such as methoxy PEG amine, HCl salt (MW of 5,000 to 20,000); hydroxyl PEG carboxyl (MW of 2,000 to 7,500); hydroxyl PEG amine, HCl salt (MW of 2,000 to 7,500); amine PEG carboxyl (MW of 2,000 to 7,500); maleimide PEG amine, TFA salt (MW 2,000 to 7,500), and poloxamers (Pluronics™). Particularly good results have been obtained using PVA as the amphiphilic emulsifier.

Preferably, both the charge modulator and the emulsifier are amphiphilic substances which, when incorporated into the NP, present chemically reactive functional groups on the NP surface, e.g., amine groups, hydroxyl groups or the like, which can be protonated at acidic pH.

The respective amounts of each NP component, based on the total NP weight, is 85.00 to 99.99 wt. %, preferably 96.00 to 98.50 wt. % of biocompatible polymer; 0.01 to 10 wt. %, preferably 0.50 to 2.00 wt. % charge modulator; and 0.05 to 5.00 wt. %, preferably 1.00 to 2.00 wt. % amphiphilic emulsifier (if present).

The preferred NP composition of the invention should be such that the net charge on NPs remains negative (at neutral pH) so that they do not interact with serum proteins.

As used herein, the term "nanoparticle" refers to a particle having a matrix-type structure with a size of less than about 1,000 nanometers. When the NP includes a bioactive agent, the bioactive agent is entangled or embedded in the matrix-type structure of the NP. The particle size of the NPs of the present invention is generally in the range of 10 to 300 nm in diameter, more preferably 100 nm diameter or smaller. NPs include particles adapted to contain a therapeutic/diagnostic agent that is to be released within a mammalian body.

The term "bioactive agent", as used herein refers to a wide array of different substances useful in the therapeutic, prophylactic or diagnostic treatment of humans or animals. Such agents include low molecular weight drugs, therapeutic polypeptides, or nucleic acid molecules (DNA/RNA). Representative examples of low molecular weight drugs are tumoricidal or anti-cancer agents (e.g., doxorubicin, paclitaxel), anti-inflammatory agents (steroids), anti-proliferation agents, analgesic agents, antibacterial agents, antiviral agents, antifungal agents, antiparasitic agents, proteins, toxins, enzymes, hormones, neurotransmitters, glycoproteins, immunoglobulins, immunomodulators, polysaccharides, cell receptor binding molecules, anti-glaucomic agents, mydriatic compounds and local anesthetics. The polypeptide may be a peptide or protein, including enzymes or antigen molecules, such as somatotropin, tetanus toxoid, influenza virus and or the like. Also, drug combinations can be used in carrying out the invention, if desired.

The NPs described herein may also be used for the delivery of a diagnostic agent, which may be any compound or substance capable of facilitating the detection, determination or analysis of a physiological condition or state by an in vivo or in vitro test. Representative examples of diagnostic agents for use in the practice of this invention are dyes and fluorescent compounds, radio-isotopes, contrast agents.

Specific examples of the foregoing categories of bioactive agent are provided in International Patent Application Pub. No. WO 98/56348 of Kabanov et al, Compositions for Delivery of Biological Agents and Methods for the Preparations Thereof.

As used herein, the terms "peptide", "protein", and "polypeptide" are used interchangeably and refer to a compound made up of a chain of amino acid residues linked by peptide bonds. The sequence for peptides is given in the order from the amino terminus to the carboxyl terminus.

The term "delivery" as used herein refers to the introduction of foreign agent (i.e., the bioactive component(s) of a NP) into cells.

The term "treating" as used herein means the prevention, reduction, partial or complete alleviation or cure of a disease.

The term "administration" as used herein means the introduction of a foreign agent (i.e., the bioactive component(s) of a NP) into a cell. The term is intended to be synonymous with the term "delivery". Administration also refers to the methods of delivery of the NPs of the invention (e.g., routes of administration such as, without limitation, intravenous, intra-arterial, intramuscular, subcutaneous, intrasynovial, infusion, sublingual, transdermal, oral, or topical). The preferred method of delivery is to the blood vessel (e.g., artery or vein) or in particular applications to the carotid, coronary, femoral, renal, or cerebral artery, depending on the site of injury.

As used herein, the term "effective amount" refers to an amount of bioactive agent sufficient to bring about the treatment for which such agent is administered.

The term "patient" as used herein refers to any vertebrate animal, preferably a mammal, and more preferably a human.

The following sections describe the invention in further detail, with reference to specific embodiments. These are representative embodiments of the invention which are provided for illustrative purposes only, and which should not be regarded as limiting the invention in any way.

Materials

Poly DL-lactide-co-glycolide (PLGA, 50:50 lactide-glycolide ratio, inherent viscosity 1.32 dL/g in hexafluoro-isopropanol at 30° C.) was purchased from Birmingham Polymers (Birmingham, Ala., USA). Bovine serum albumin (BSA, Fraction V), poly vinyl alcohol (PVA, average molecular weight 30,000-70,000), poly-L-lysine hydro bromide (PLL.HBr, average molecular weight 30,000-70,000), peroxidase from horse radish (HRP, Type VI-A, molecular weight 44,000), and SIGMAFAST™ OPD were purchased from Sigma (St. Louis, Mo., USA). Texas Red® labeled dextran (molecular weight 10,000; lysine fixable), Texas Red® labeled transferrin, Prolong™ Gold antifade reagent and all cell culture reagents were purchased from Invitrogen (Carlsbad, Calif., USA). 6-Coumarin was purchased from Polysciences Inc. (Warrington, Pa., USA). Chambered cover glass slides were purchased from LabTek (Rochester, N.Y., USA). BCA protein assay kit was purchased from Pierce (Rockford, Ill., USA). AFM probe tips were purchased from Veeco/Digital Instruments Inc. (Santa Barbara, Calif., USA). All other chemicals and reagents were from Fisher Scientific (Pittsburgh, Pa., USA). All aqueous solutions were prepared with deionized and distilled water (Labconco Co., Kansas City, Mo.).

Methods
Cell Culture
Cell Line Used in the Study:

The human breast carcinoma cell line (MDA-MB-435S) was used in all the cell culture studies. Cells were grown in Dulbecco's modified Eagle's Medium (DMEM) supplemented with 10% heat inactivated fetal bovine serum (FBS) and incubated in a humidified incubator in 5% $CO_2$ at 37° C. The medium was changed every alternate day.

Cell Culture for AFM Studies:

MDA-MB-435S breast cancer cells were grown on PLL coated chambered glass slides in a humidified incubator in 5% $CO_2$ at 37° C. in Dubbecco's Modified Eagle's Medium (DMEM) supplemented with 10% heat inactivated fetal bovine serum (FBS). This was done to ensure that the adherent cells were grown on a surface with high cell-substrate interaction so that the cells do not detach while imaging. Typically, cells from passage 4-8 were used in all the experiments. For experiments with live cells, cells were washed three times with serum free cell culture medium (SFM) just before the experiments and imaged (in the presence of SFM containing 25 mM HEPES) using AFM. Addition of HEPES provides supplementary buffering to the cell culture medium and prevents pH changes when cells are maintained outside the $CO_2$ incubator at RT for experiments.

Cell Culture for Confocal Studies:

MDA-MB-435S cells were grown on cover-slips in a humidified incubator in 5% $CO_2$ at 37° C. in DMEM supplemented with 10% FBS.

Formulation and Characterization of NPs
Formulation of NPs:

NPs containing BSA as a model protein and 6-coumarin as a fluorescent marker were formulated with DL-PGLA using a double emulsion solvent evaporation technique, as described previously [3]. In brief, an aqueous solution of BSA (10 mg BSA dissolved in 150 µl of water) was emulsified into 1 ml of the polymer solution (30 mg polymer in 1 ml chloroform, containing 18 microgram of 6-coumarin) using a probe sonicator (55 W for 2 min) (Sonicator XL, Misonix, N.Y.). This primary water-in-oil emulsion was emulsified into 8 ml of an aqueous solution of polyvinyl alcohol (PVA: an emulsifier) and poly-L-lysine (PLL: charge modulator) using the probe sonicator as above for 5 min to form a multiple water-in-oil-in-water emulsion. The multiple emulsion was then stirred at room temperature for ~18 hrs and then under vacuum for one hour to evaporate chloroform completely. NPs with entrapped protein were recovered by ultracentrifugation (30,000 rpm for 20 min at 4° C., Optima™ LE-80K, Beckman, Palo Alto, Calif.) washed twice with distilled water to remove unentrapped PVA, PLL and protein. The particles were suspended in water and lyophilized for 48 hrs to form a dry powder.

NPs entrapping HRP were prepared in the same manner, with the exception of addition of 6-coumarin in polymer solution. A solution of HRP (5 mg) and BSA (10 mg) in phosphate buffer (pH 6.0) was used as the first aqueous phase.

Characterization of NPs:
Particle Size:

Particle size and polydispersity of NPs was determined using a Zeta Plus™ particle size analyzer. The concentration of PVA and PLL in the external aqueous phase was varied to optimize the formulation of NPs to modulate the surface charge of NPs. A suspension of NPs (0.1 mg/ml) was prepared in double-distilled water and sonicated for 30 s on an ice bath.

Zeta Potential:

Zeta potential of NPs was measured using Zeta Plus™ zeta potential analyzer. NPs were suspended in a buffer of pH 7.0 prepared using 1 mM hydroxy ethyl piperazine ethane sulfonic acid (HEPES) solution and adjusting pH with 0.1N sodium hydroxide or hydrochloric acid solutions.

Protein Loading:

The amount of protein loaded into NPs was determined in an indirect manner from the total amount of protein added in the formulation and the protein that was not encapsulated into the NPs. The concentration of protein in the washings was calculated by using the BCA protein assay kit with the washings from the control NPs functioning as a blank. HRP loading in NPs was determined in a similar fashion by using activity assay (OPD colorimetric assay) of HRP.

FTIR of NPs:

NPs were evaluated for the presence of different functional groups on the surface by means of Fourier Transform Infra-Red (FTIR) spectroscopy. The IR instrument-SenslR FT-IR microscope with ATR objective, manufactured by Smiths Detection (Danbury, Conn.) was used. 64 scans of the diamond ATR objective background were acquired prior to each sample. Each sample of NPs was placed on a microscope slide. The ATR objective was used on the microscope to make contact with each sample (approx. 100 µm diameter observed area). 64 scans were acquired for each sample, at a 4 cm$^{-1}$ resolution. The diamond tip was cleaned with methanol prior to taking a new background and sample acquisition.

Instrumentation/Atomic Force Microscopy (AFM)

A commercial Molecular Force Probe 3D system (MFP-3D, Asylum Research, Santa Barbara, Calif.) was used for all studies involving atomic force microscopy. Silicon nitride ($Si_3N_4$) AFM probe tips were washed by immersing in ethanol for 30 min and then activated by UV treatment for 30 min. Activated tips were used for imaging and coated with NP formulations for force spectroscopy. Spring constants for each cantilever were determined using the thermal noise method with the MFP-3D instrument. All experiments were performed at ambient temperature and atmospheric pressure.

AFM Imaging of NPs

Mica surface modified with 1-(3-aminopropyl) silatrane (APS-mica) was used for this experiment. Procedures for mica modification with APS and sample preparation have been described previously [9]. Briefly, NPs suspended in phosphate buffer (pH 7.0) were placed as a drop on the APS-mica surface, and allowed to incubate at room temperature for 2 min. The NP suspensions were washed off from the mica surface, followed by rinsing of the surface with deionized water and drying in presence of Argon gas. Images were acquired in air with MFP-3D instrument operating in the AC (tapping) mode. Tapping Mode Etched Silicon Probes (TESP, Veeco/Digital Instruments, Inc.) with a spring constant of 40 pN/nm and a resonance frequency of 320 kHz were used.

Time-Lapse AFM Imaging of Live Cells

AFM can be used to visualize surface-dependent molecular events in 3-dimensions on a nanometer scale in aqueous environment [10-13]. AFM has been employed in numerous studies to image cells both in living state and after fixation of cells [14-16]. Imaging fixed cells (in air) is relatively easier than imaging live cells (in liquid) due to the increased hardness of the cells after dehydration with fixatives. However, fixation of cells may introduce image artifacts such as depressions, pits or folds as a result of cross-linking of the membrane proteins, and cannot be used to image the dynamic changes in the topology of cells. In order to monitor the dynamic changes on cell surface as a result of incubation with NPs, AFM imaging was performed on live cells incubated with the two kinds of NPs. MDA-MB-435S cells were grown as mentioned earlier. AFM images of the cell surface were acquired in AC (tapping) mode in liquid (SFM) using clean $Si_3N_4$ probe tips with spring constants of 40-60 pN/nm and average resonance frequency of 9 kHz. In tapping mode, a high frequency z-oscillation of the tip is used with the normal x-y scanning, which causes the probe tip to be only in intermittent contact with cells; thus minimizing the destructive shear forces [17 and 18]. Briefly, the glass slide on which the cells were grown was placed on the x-y piezo stage of MFP-3D instrument. With the help of view from the optical objective (placed at the bottom of MFP-3D instrument), cantilevers were positioned above the cells. A 90×90 micrometer image was acquired to image and locate individual cells. The cantilever was then moved to the surface of any of the cells imaged. Further, 2×2 µm images were acquired at the cell surface in AC (tapping) mode in the presence of SFM at a minimal scan rate of 2 Hz. NPs suspended in SFM (at a concentration of 80 µg/ml) were added onto the cells for AFM imaging. Time-lapse images were acquired at the same surface of cells after incubation with NPs. The average time for acquisition of one 2×2 µm image was 5 min and time-lapse images were acquired for 20 minutes on each cell surface. Image acquisition was done in the height, amplitude and phase modes for each time point. After finishing 20 min of time-lapse imaging, the probes were used to image cells on a new slide. The image of cells appeared similar to that at the starting of the experiments. This confirmed that there was no contamination of the tip with the NPs or cell proteins even after 20 min of continuous imaging. However, the slide of cells and the AFM probe tip was always changed before imaging for the second type of NPs. Cells imaged with AFM were tested for viability using Trypan-blue dye exclusion method. This helped to confirm that the cells remained in a viable state after the 30 min of imaging experiments.

TABLE 1

| Incubation conditions | % viable cells determined using Trypan blue exclusion |
|---|---|
| Cells incubated with HEPES containing SFM at 37° C./5% $CO_2$ | 98 ± 1.5 |
| Cells in HEPES containing SFM at RT before imaging | 97 ± 1.0 |
| Cells in HEPES containing SFM at RT after imaging | 96 ± 2.1 |

Further, it has been reported that AFM imaged live cells remained viable up to 48 hr post-imaging without any significant cell damage or cell death [18].

Figure 6:
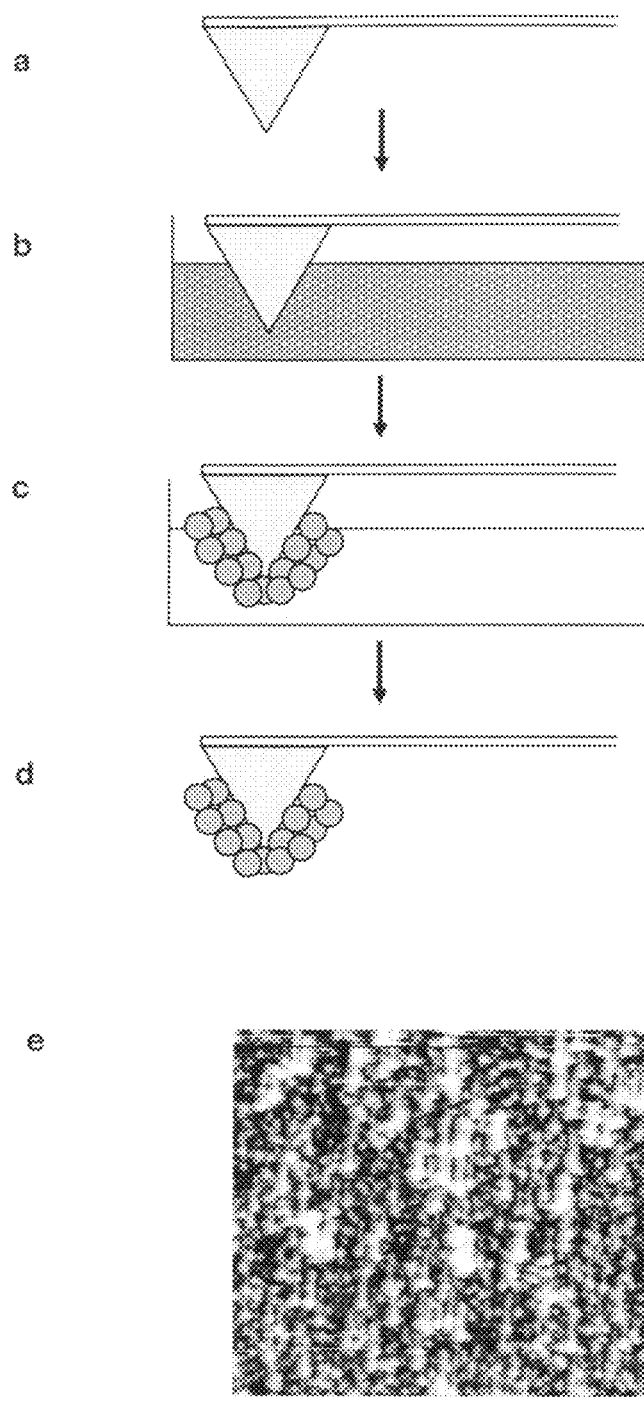
FIG. 6 is a schematic representation of the process of coating of AFM tip with NPs.

Coating of AFM Tip with NPs $Si_3N_4$ AFM probe tips were washed and activated as described above, and their spring constants were measured using the thermal noise method. Activated probe tips and freshly cleaved mica were treated with the double emulsion of the different kinds of formulation of NPs. The double emulsions were prepared as described above in the NP formulation procedure. Mica and probes were placed in the emulsions and chloroform (present in the emulsion) was allowed to evaporate under vacuum for 3 hrs. This allowed the formation of NPs directly on the mica surface and the probe tips, following which the mica and probe tips were washed three times with deionized water and dried in Argon gas. A schematic representation of the process of modification of AFM tip with NPs is shown in FIG. 6 (FIG. 6a-d). Scanning electron microscopy (SEM) of the AFM tips was used to confirm the modification of tips with NPs.

Force Measurements

Figure 7A:
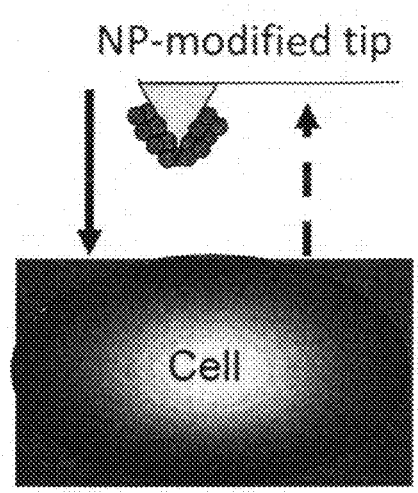
FIG. 7a is a schematic representation of the setup for collection of force curves on cell membrane with AFM tip coated with NPs.
Figure 7B:
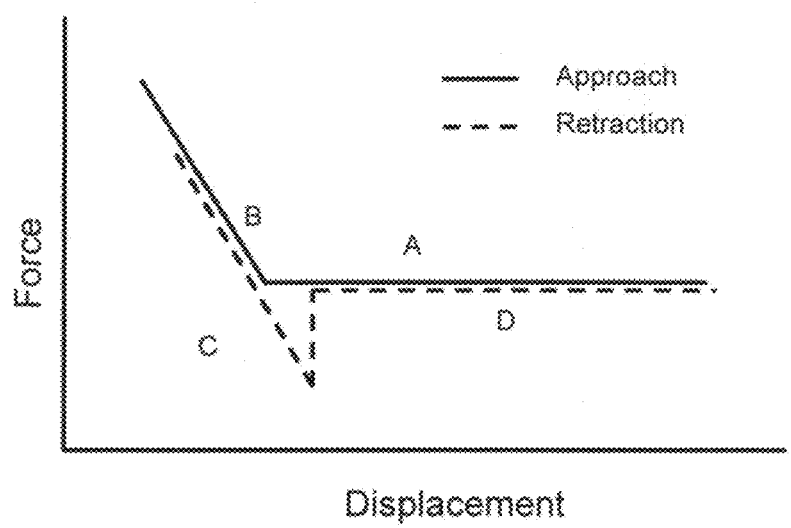
FIG. 7b is a diagram of a typical force curve (solid line: approach curve; dash line: retraction curve). The x axis represents the displacement and the y axis represents the force calculated as the product of spring constant of the cantilever and the cantilever deflection.

Force-distance measurements were performed on the surface of cells grown on glass slides in the presence of SFM, using the AFM probe tips coated with different NP formulations. The NPs were deposited/formed on the AFM probe tips and force of interaction between these probes and cells was directly measured using AFM force spectroscopy as a function of their separation distance (FIGS. 7a and b). All measurements were performed with MFP-3D instrument operating in the contact mode at ambient temperature. MDA-MB cells (typically from passage 4-8) were grown on glass slides as mentioned before at a cell density of 90%. This was done to minimize any variations in the measurements, since the morphology and visco-elasticity of cells differs with the growing conditions and can alter the orientation of the molecules on cell surface responsible for adhesion to the NPs [1,9]. Before starting the experiments, the cells were washed with SFM to ensure that proteins present in serum do not complicate the results from the force measurements.

Prior to using the NP coated AFM probe tips, their spring constants were measured again and tips with spring constants of 40-60 pN/nm only were used for the experiments. The cantilevers were carefully positioned on top of the cells, visualized with the help of the optical view. NP coated probe tips were approached to the cell surface and force measurements were recorded at a loading rate of $2.8 \times 10^4$ pN/s (loading rate is the product of cantilever spring constant and retraction velocity). Force curves were collected on multiple cells, typically 50-60 force curves were measured on a single cell, and a total of 500-600 force curves were collected for tips coated with each kind of NP formulation. During the entire experiment, cells were monitored with the help of the optical objective equipped with the AFM.

Data Analysis

All height mode images collected on the surface of cells were processed for height and surface roughness measurements, as well as for statistical treatment of the data with Femtoscan software (Advanced Technologies Center, Moscow, Russia). For analysis of force curves, the IGOR Pro software package was used. Typically, the forces of interaction obtained from 500 force curves were compiled in force distribution histograms. The most probable force of interaction is defined by the maximum of the Gaussian fit to each histogram. Probability of interaction of NP-coated tip and cell surface was calculated as the percentage of force curves which show interactive forces of the total (n=500) forces collected with the tip.

Cellular Uptake of NPs

MDA-MB-435S cells were seeded at 40,000 cells/mL/well in 24-well plates (Falcon, Becton Dickinson, N.J.) and allowed to attach for 24-36 h. To determine the NP uptake, cells were incubated with a suspension of NPs in cell culture medium. Cells harvested at appropriate times, were washed three times with cold phosphate buffered saline (PBS, pH 7.4, 154 mM), and lysed by incubating cells with 0.1 mL of 1% aqueous solution of TritonX-100 for 30 min at 37° C. The cell lysates were processed and analysed for the levels of NPs by high-performance liquid chromatography (HPLC) procedure, as described previously [20]. Results of NP uptake were expressed as µg of NPs per mg of total cell protein. For the cellular uptake study, a formulation of NPs containing a fluorescent dye (6-coumarin) was used. The incorporated dye acts as a probe for NPs and hence can be used to quantitatively determine the cellular uptake of NPs [21], and to study their intracellular distribution using confocal microscopy.

To study the dose-dependent cellular uptake of NPs, cells were incubated with different concentrations of NP suspension (25-1000 µg/mL) for 2 h. Time-dependent cellular uptake of NPs was determined by incubating cells with a suspension of NPs (100 µg/mL) for different time periods. Exocytosis of NPs was followed by incubating the cells with NPs (100 µg/mL) for 2 h, followed by washing off of the uninternalized NPs with PBS for two times. The intracellular level of NPs after washing of the cells was taken as the zero time point value. Cells in other 24-well plates were then incubated with fresh cell culture medium. At different time intervals, the medium was removed, cells were washed two times with PBS, lysed, and the intracellular NP levels were analysed to determine the fraction of internalized NPs that were retained inside the cells. NP fraction that exocytosed into the medium was also quantified for each time point to determine the mass balance.

Intracellular Trafficking of NPs

Cells grown on cover-slips were incubated with fluorescently labeled NPs (100 µg/mL) for 1 h at 4° C. to allow binding of NPs on the cell membrane. The medium containing NPs was then removed and replaced with fresh cell culture medium and cells were further incubated at 37° C. for different time intervals (5-60 min) to chase the NPs into various intracellular compartments, following their endocytosis. To label early endosomes (EE), the endosomal marker Texas Red® transferrin (100 µg/ml) was added to the cells 5 min before each time point. To label late endosomes (LE), cells were pre-incubated with lysine-fixable Texas Red® dextran (0.5 mg/ml) for 15 min, followed by chasing the label into LE via incubation in dextran-free medium for 5 min. At each time point, cells were washed two times with ice-cold PBS, fixed with 4% paraformaldehyde solution, washed twice with PBS, and mounted on glass slides using Prolong™ Gold antifade medium. These fixed cells were observed under a confocal microscope (Zeiss LSM410, Carl Zeiss Microimaging, Thornwood, N.Y.) equipped with argon-krypton laser. Serial z-sections of 1 µm thickness were collected for both 488 nm filter (fluorescein: 6-coumarin labeled NPs) and 568 nm filter (rhodamine: Texas red transferrin). The confocal images were processed and analysed for pixel areas using ImageJ software (NIH). The pixel area for images collected using fluorescein filter determined the cellular content of NPs; pixel areas for rhodamine filter images determined the endosomal content of the cell; and the pixel areas from co-localized images generated using the ImageJ software determined the NPs present in the endosomal compartment of the cell. To determine the fraction of NPs that escape into the cytosolic compartment, the pixel areas of co-localized NPs was subtracted from that of the total cellular content of NPs.

To perform all these calculations, first the pixel areas for cellular (fluorescein filter) and endosomal (co-localized with endosomes) content of NPs were determined in each x-y plane and were denoted as $A_z$ (cellular) and $A_z$ (endosomal). The fraction of NPs that escaped into the cytosol was indicated by the pixel area $A_z$ (cytosol) and was calculated as $A_z$ (cytosol)=$[A_z$ (cellular)$]-[A_z$ (endosomal)$]$. The values of $A_z$ (cytosol) and $A_z$ (endosomal) were summed up for all the z-sections and were denoted as A (cytosol) and A (endosomal), respectively. These total pixel areas indicated the total amount of NPs present in the cytoplasmic and endosomal compartments of the cell. For each time point, data from 15 cells were used to evaluate the dynamics of intracellular trafficking of NPs (FIG. 9d). Before the actual experiments with cells were performed, control experiments were carried out to ascertain a linear relationship between the amount of NPs and the pixel areas obtained in confocal images. For this step, 20 µl of NP suspension (of various concentrations) was placed between two coverslips and imaged using a confocal microscope. The images were processed as mentioned previously, and pixel areas were plotted against concentration of NPs. This calibration curve indicated a linear relationship between the amount of NPs and the pixel areas (data not shown).

Intracellular Delivery of a Model Protein (HRP) Using NPs

To study intracellular delivery of HRP using NPs, MDA-MB-435S cells were seeded at 25,000 cells/mL/well in 24-well plates (Falcon®, Becton Dickinson, N.J.) and allowed to attach for 24 h. For investigating the sustained activity of HRP enzyme when loaded with NPs in comparison to HRP solution: cells were incubated with 4 µg/mL HRP (dissolved in cell culture medium); and 100 µg/mL of HRP-loaded NPs (equivalent to 4 µg HRP) for 24 h. Medium was changed after 24 h and then every alternate day. After 1, 3, and 5 days, cells were washed twice with ice-cold PBS, and lysed on ice in Tris-HCl buffer (pH=7.6, 50 mM) containing 1% TritonX-100. Cell lysates were centrifuged at 14,000 rpm, 4° C. for 10 minutes and the supernatants were analysed for HRP activity using the SIGMAFAS™ OPD (colorimetric assay). HRP concentrations in lysates were determined by comparing HRP activity in the lysate to a standard curve of purified HRP. The comparison of a standard curve of purified HRP prepared in Tris-HCl buffer (pH=7.6, 50 mM) containing 1% TritonX-100 to that prepared in the enzyme-free cell lysates, indicated that the cell lysate components did not affect the determination of enzyme activity. Amount of active HRP was normalized to the total cell protein and expressed as ng/mg cell protein.

A dose-dependent study was performed in the same manner except that cells were incubated with different doses of HRP solution (4, 8, 12, 16 µg) and HRP-loaded NPs (equivalent to HRP dose-100, 200, 300, and 400 µg) for 24 h. Medium was changed after 24 h and then every alternate day. After 5 days cells were washed, lysed and HRP levels were determined by activity assay. Amount of active HRP was normalized to the total cell protein and expressed as ng/mg cell protein.

Statistical Analysis

Statistical analysis was performed using the Student's t-test and differences were considered significant at p values of <0.05.

Results

Formulation and Characterization of NPs

As can be seen in Table 2, below, a gradual increase in the particle size of NPs was observed as the concentration of PVA (emulsifier) in the formulation was reduced. PVA acts as an emulsifier during the formulation of NPs by the double emulsion method. Sahoo et al. have previously shown that viscosity of PVA solution decreases with decreasing PVA concentration [7]. This reduced viscosity would result in the formation of relatively larger droplet size during emulsification, leading to formation of larger sized NPs with higher polydispersity index. The mean hydrodynamic particle size of NPs increased from 290 nm to 430 nm with a decrease in PVA concentration from 2.5% to 0.5% w/v. The polydispersity index of NPs preparation with 2.5% w/v PVA was 0.08, and it showed an increase to 0.25 for NPs preparation with 0.5% w/v PVA solution.

NPs prepared with high concentration of PLL (1.5-2.0% w/v) demonstrated a positive zeta potential at neutral pH; however, NPs prepared with low concentration of PLL were anionic at neutral pH. (See Table 2). PLL, being amphiphilic, anchors on the PLGA polymer via its hydrophobic ends, and thus shields the negative charge of the PLGA NPs. The hydrophobic segments of PVA and PLL penetrate into the polymeric matrix and remain entrapped in the PLGA matrix, thus presenting hydroxyl and amino groups on the surface of NPs (FIG. 1b).

TABLE 2

| NP Formulation | Amt of PVA (mg) used in 8 ml | Amt of PLL (mg) used in 8 ml | Particle size (nm) | Polydispersity | Zeta potential (pH = 7) |
|---|---|---|---|---|---|
| Unmodified NP | 200 | 0.0 | 296.2 ± 5.94 | 0.08 ± 0.03 | −10.5 |
| Modified NP 1 | 160 | 40 | 310.2 ± 2.30 | 0.18 ± 0.02 | −9.6 |
| Modified NP 2 | 120 | 80 | 377.0 ± 6.84 | 0.22 ± 0.03 | −4.2 |
| Modified NP 3 | 80 | 120 | 390.2 ± 4.32 | 0.24 ± 0.01 | +4.0 |
| Modified NP 4 | 40 | 160 | 428.0 ± 4.50 | 0.26 ± 0.02 | +6.5 |

As previously mentioned, the preferred NP composition of the invention should be such that the net charge on NPs remains negative so that they do not interact with serum protein. See Modified NP1 and NP2 in Table 2. The NP formulation prepared with 0.5 percent PLL (Modified NP1) also gave greater cellular uptake, despite its negative charge.

Figure 1C:
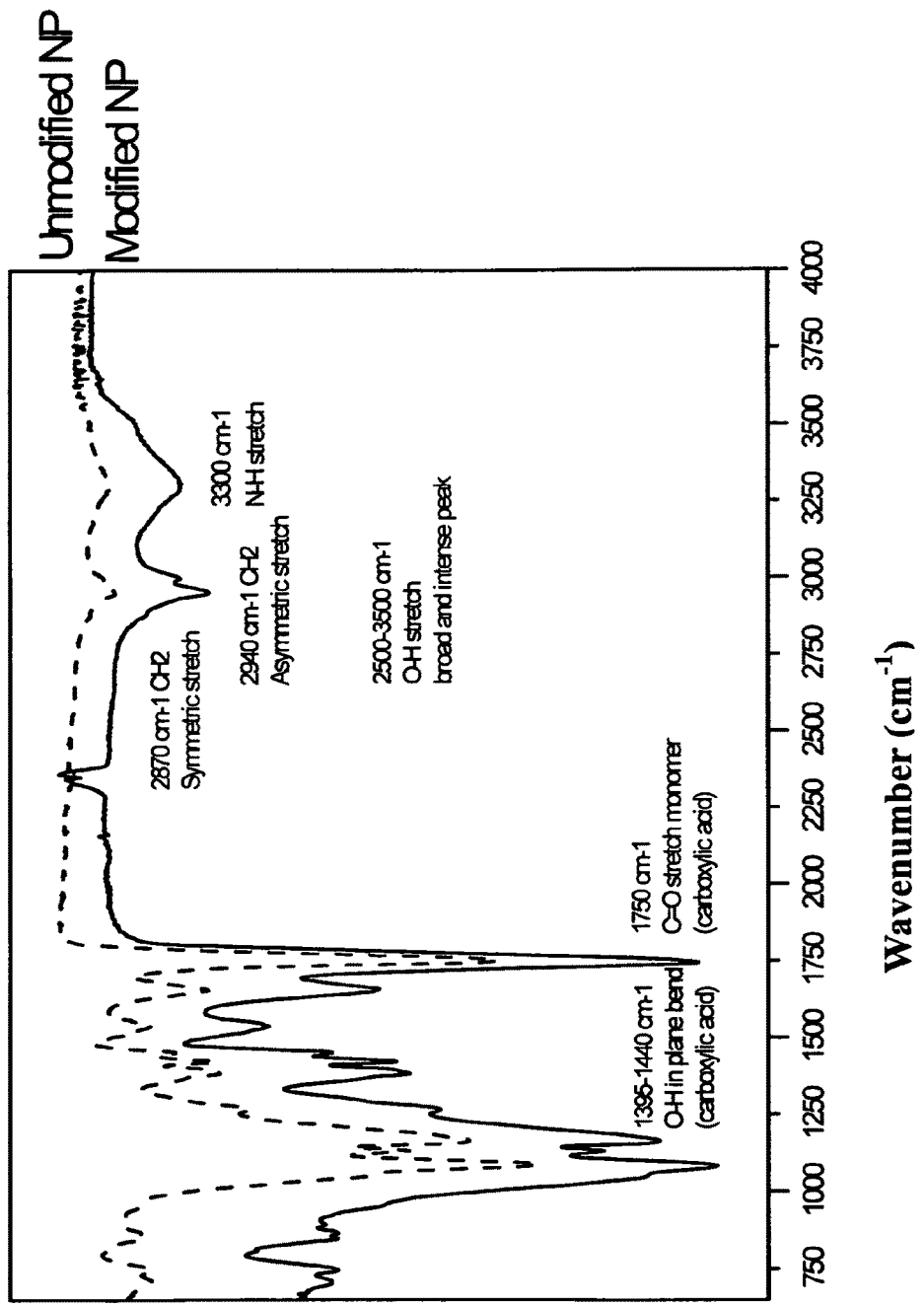
FIG. 1c is a spectra of modified and unmodified NPs.

FTIR spectroscopy of NPs using an ATR-FTIR microscope indicated characteristic N—H stretch peaks (at v=3300 cm$^{-1}$) and thus, confirmed the presence of amino groups on the surface of PLL modified NPs (FIG. 1c). HRP loading in modified and unmodified NPs was similar (4% w/w, that is 4 mg HRP present in 100 mg of NPs).

AFM Imaging of NPs

Figure 2:
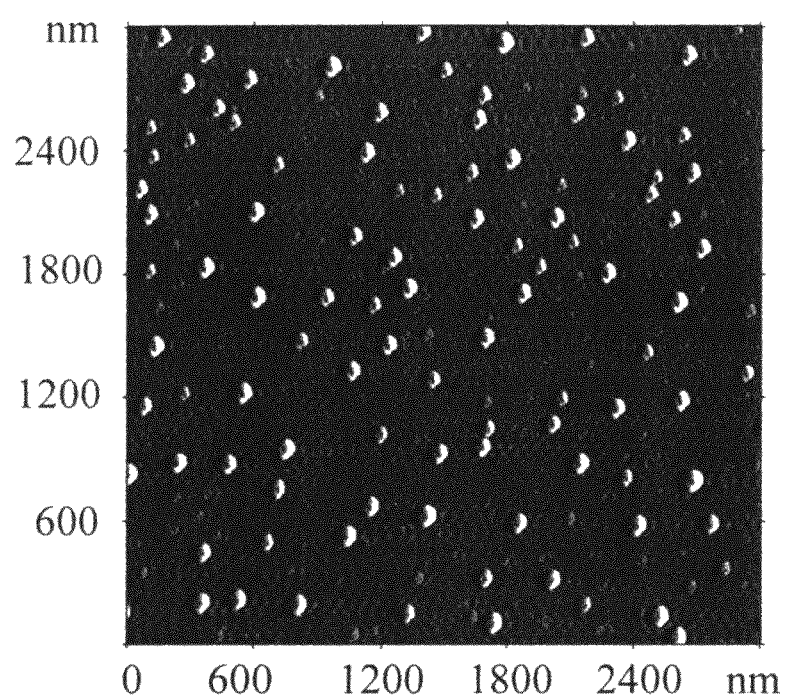
FIG. 2 is an AFM image of NPs deposited on positively charged APS-modified mica surface.

NPs (both unmodified and surface-modified NPs) were deposited on positively charged (APS-treated) mica surface, and imaged in air using AFM in AC (tapping) mode. Amplitude trace of AFM images of the NPs are shown in FIG. 2 (FIG. 2). AFM image demonstrated that the NPs are spherical in shape with a mean diameter of 50-70 nm (measured using the Femtoscan Software).

Time-Lapse AFM Imaging of Live Cells

Figure 3:
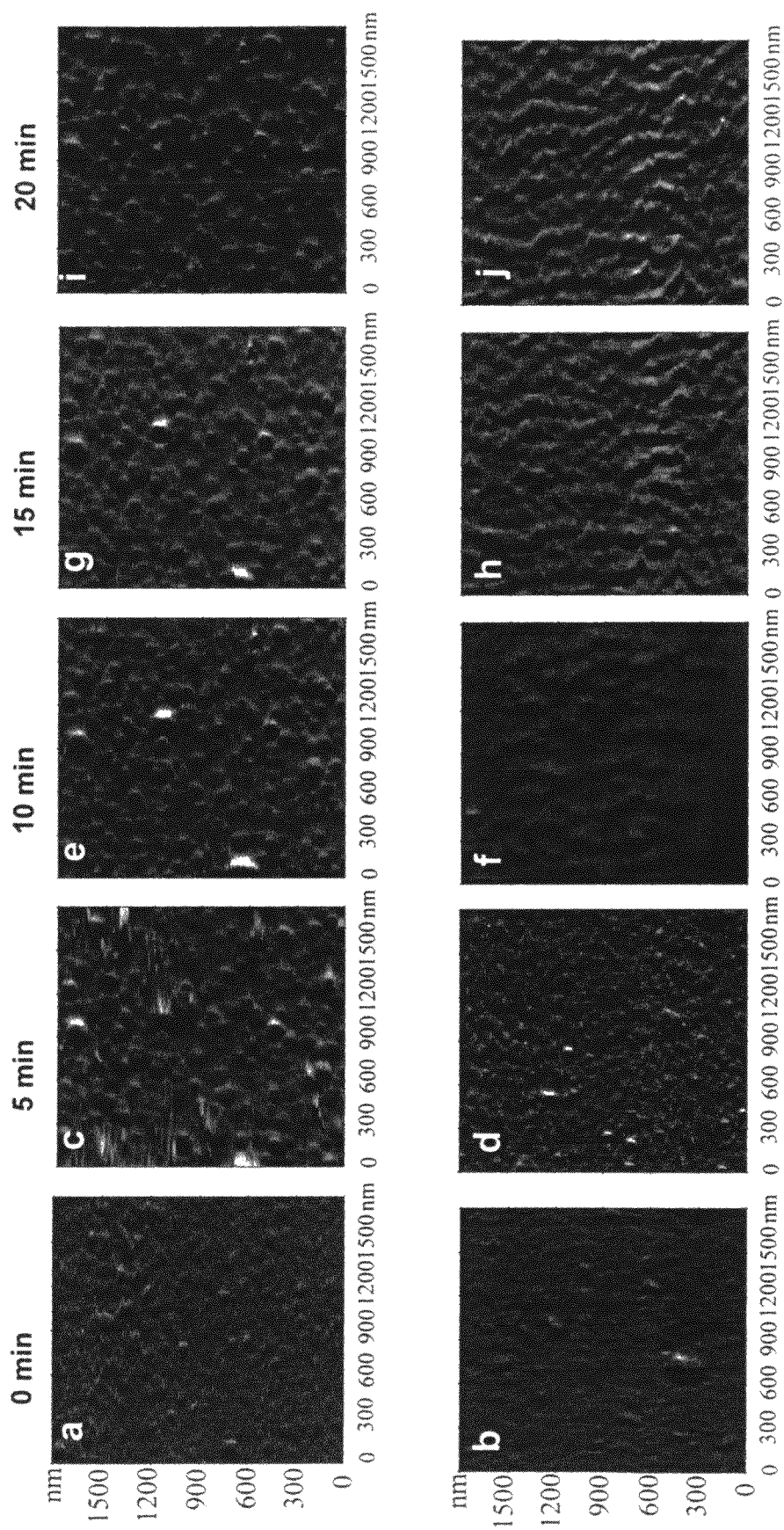
FIG. 3 shows AFM images (amplitude traces) of cell membrane incubated with unmodified NPs showing (a, c, e, g, i) and modified NPs (b, d, f, h, j) showing cell membrane before addition of NPs (a, b); and after incubation with NPs for 5 minutes (c, d); 10 minutes (e, f); 15 minutes (g, h); and 20 minutes (i, j). All images are 2×2 μm, acquired in tapping mode in liquid. Scale bar represents 300 nm.
Figure 4A:
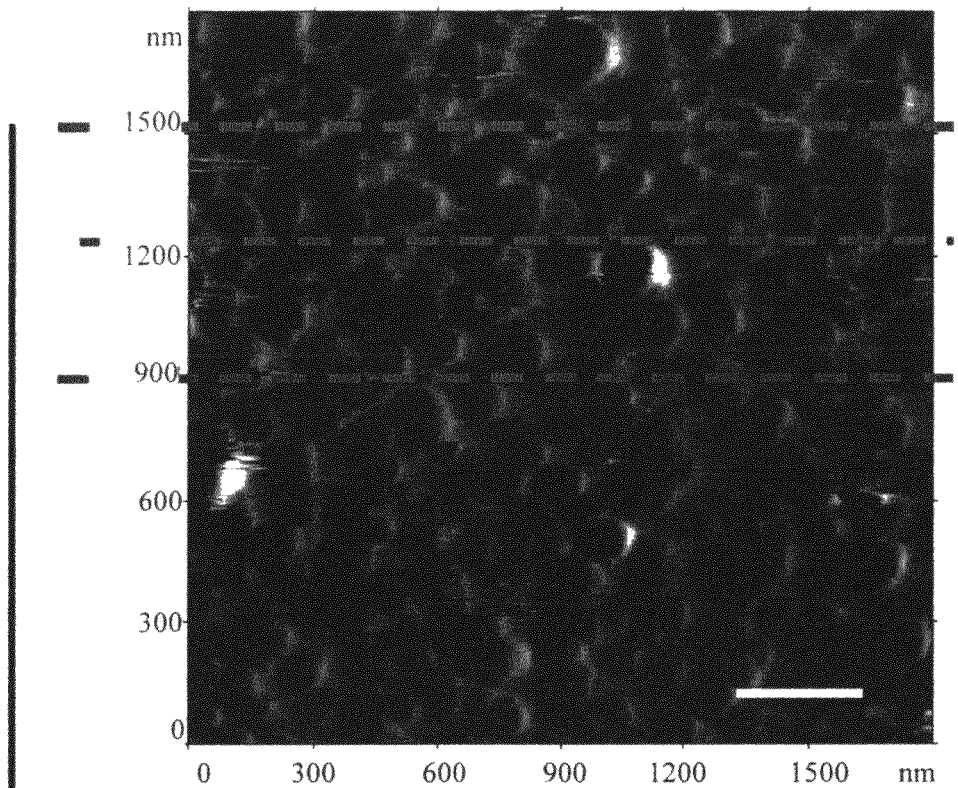
FIG. 4 shows AFM images of cell membrane topology 15 minutes after incubation with unmodified NPs (FIG. 4a) and modified NPs (FIG. 4b). Images are 2×2 μm, acquired in tapping mode in liquid. Scale bar represents 300 nm.
FIGS. 4c and 4d show section analysis along the dashed lines in a and b, respectively.
FIG. 4e is a graphical representation of average height of NPs on the cell membrane calculated from the section analysis at different times of incubation with NPs.
FIG. 4f is a graphical representation of average roughness of the cell membrane as determined using Femtoscan Software, plotted for incubation of cell membrane with unmodified and modified NPs.
Figure 4C:
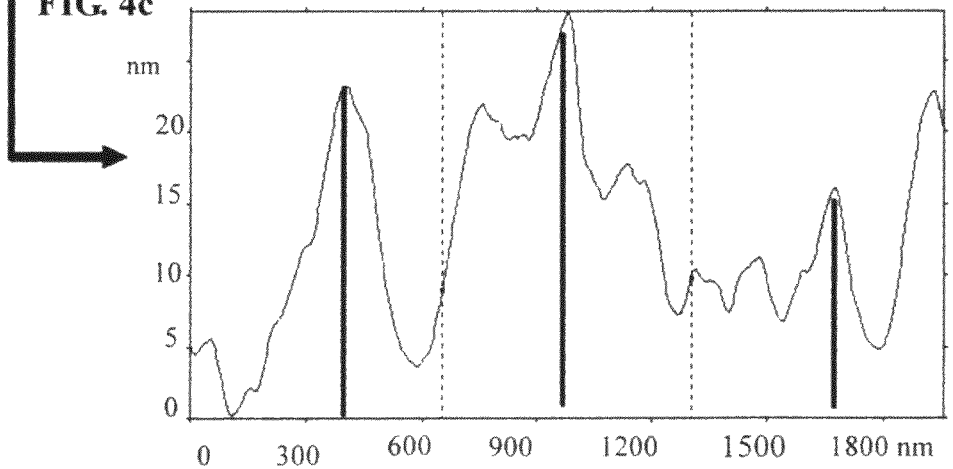
Figure 4B:
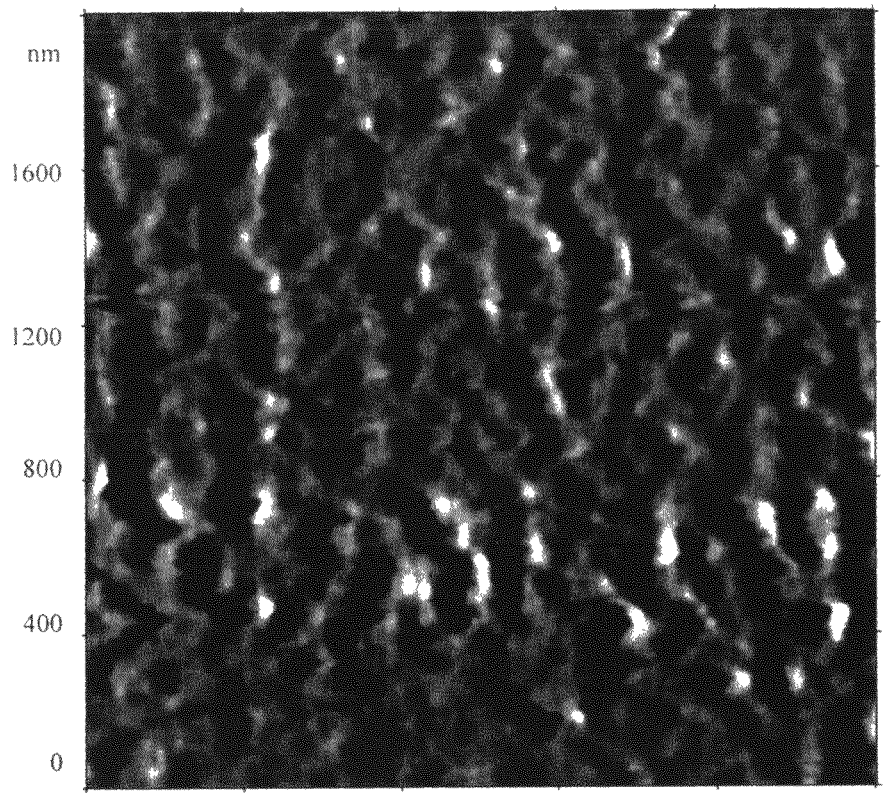
Figure 4D:
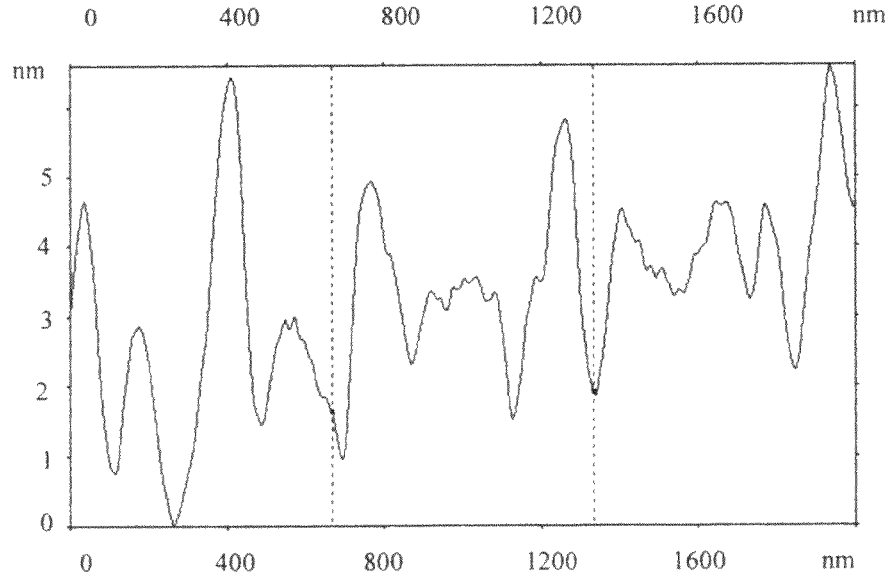
Figure 4E:
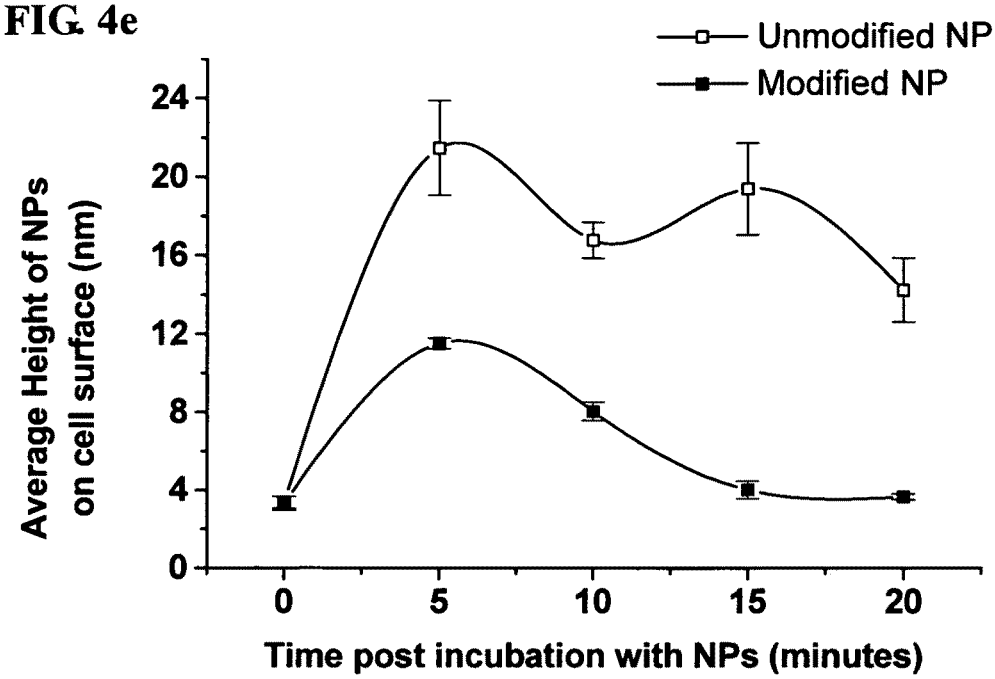
Figure 4F:
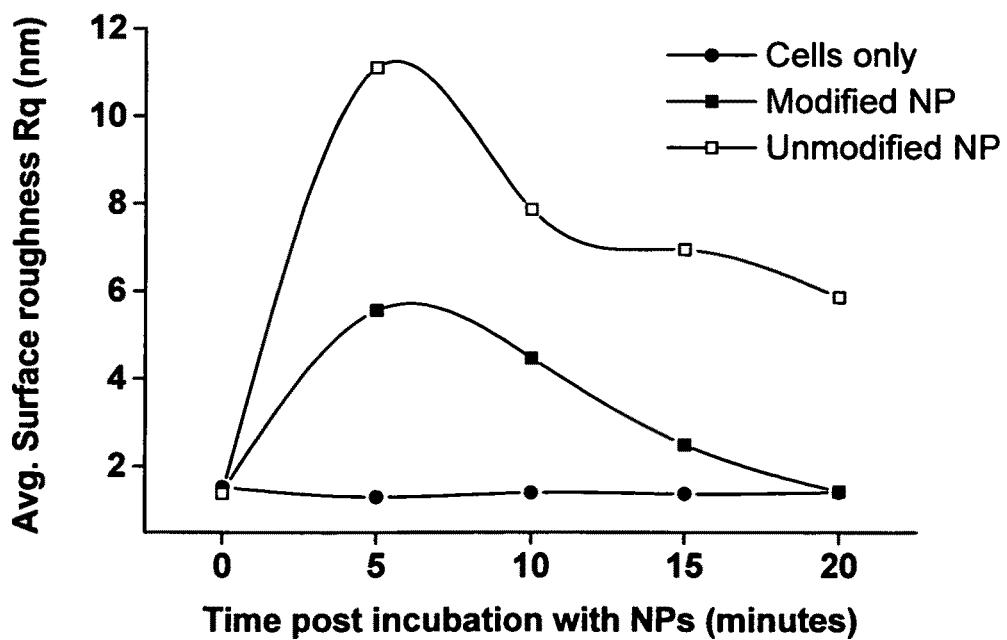
Figure 5A:
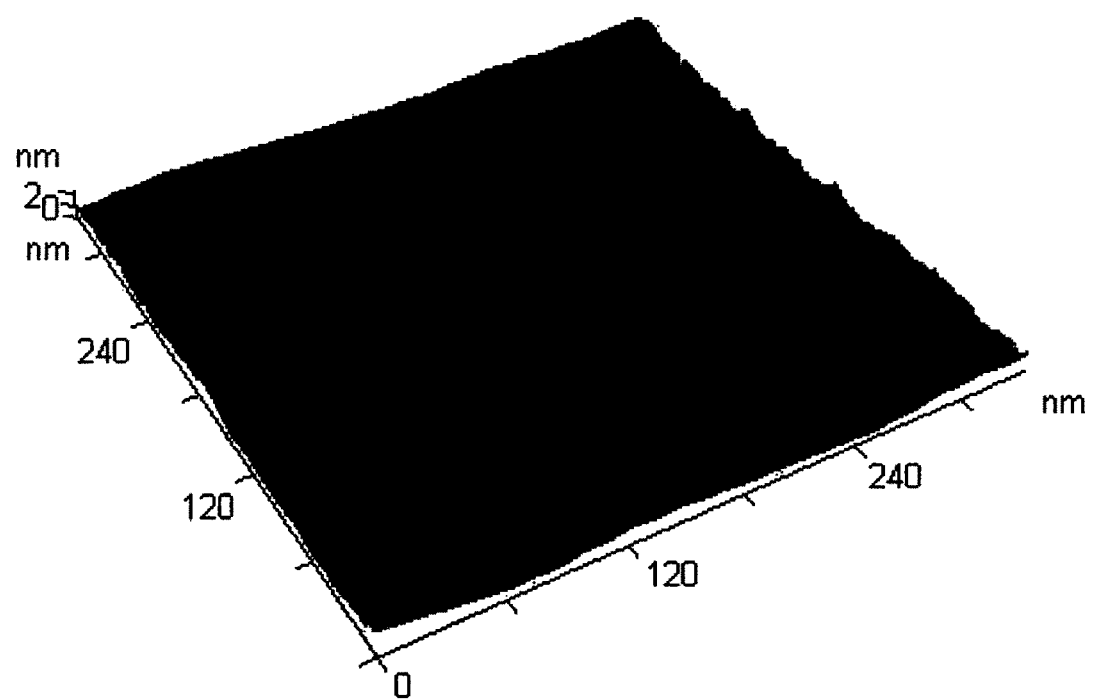
FIG. 5 shows three-dimensional images of cell membrane before (FIG. 5a), and after incubation with NPs for 10 minutes (FIG. 5b), 15 minutes (FIG. 5c), and 20 minutes (FIG. 5d). All AFM images shown in FIG. 5a-5d are cropped 400× 400 nm images from the 2×2 μm images acquired in tapping mode in liquid.
FIG. 5e shows a cell membrane having a typical pit formed on the surface of cell after incubation with NPs.
FIG. 5f shows section analysis along the dashed line in FIG. 5e. AFM image shown in FIG. 5e is cropped 300×300 nm image from the 2×2 μm image acquired in liquid. The three-dimensional views were generated using Femtoscan software.
Figure 5B:
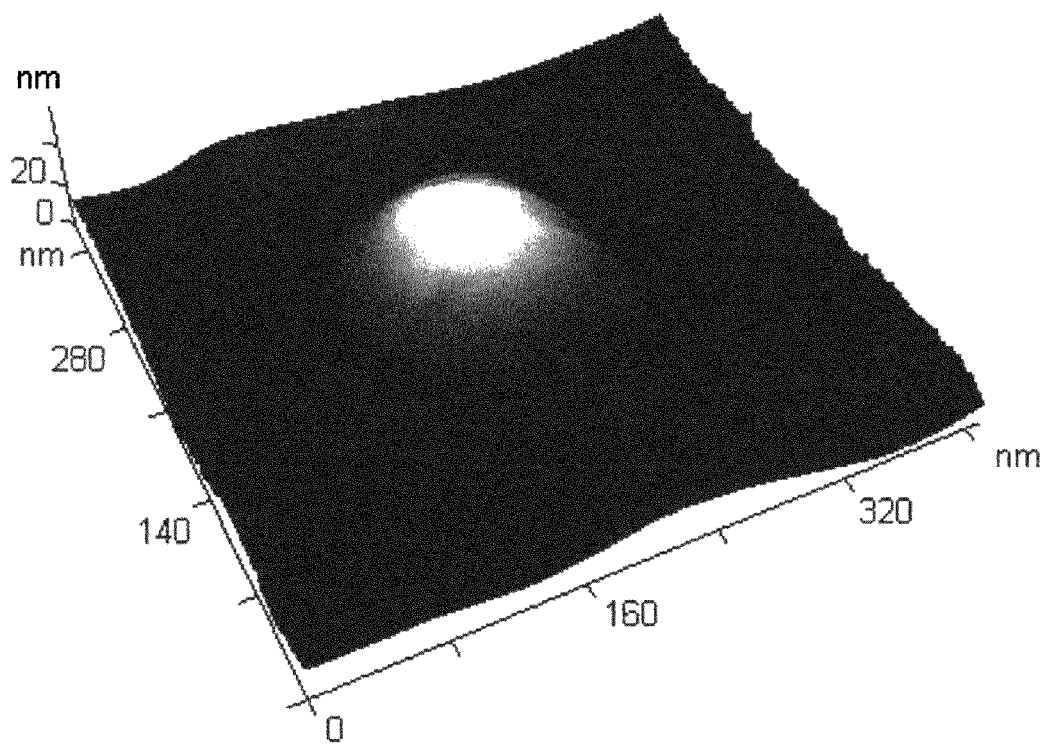
Figure 5C:
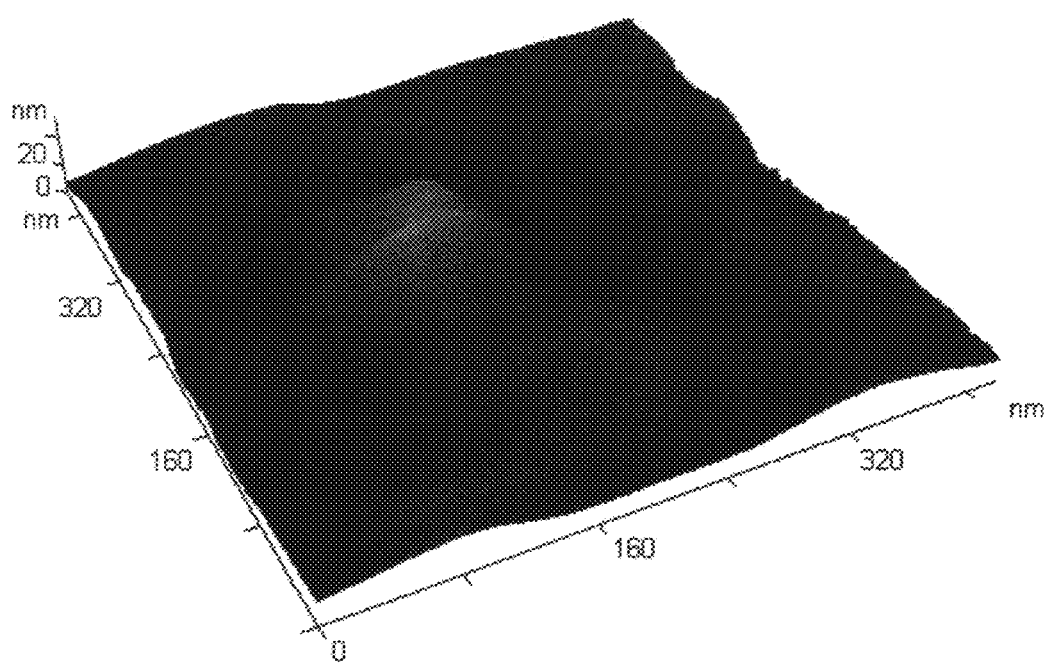
Figure 5D:
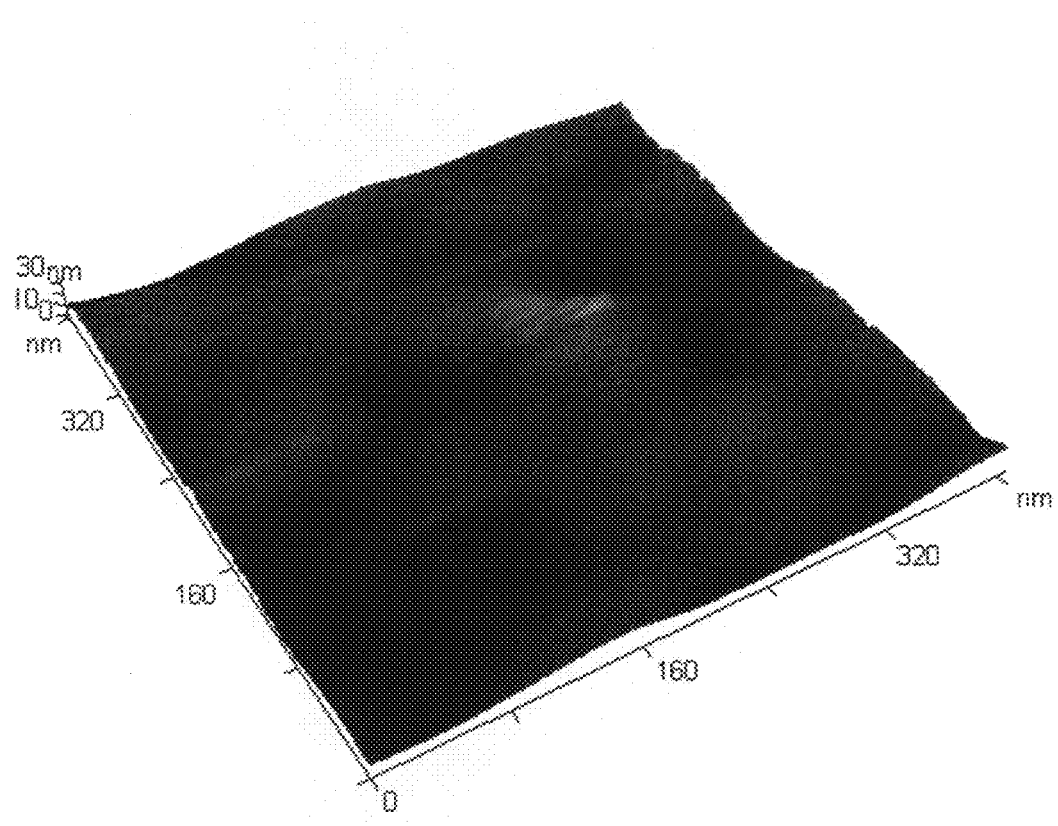
Figure 5E:
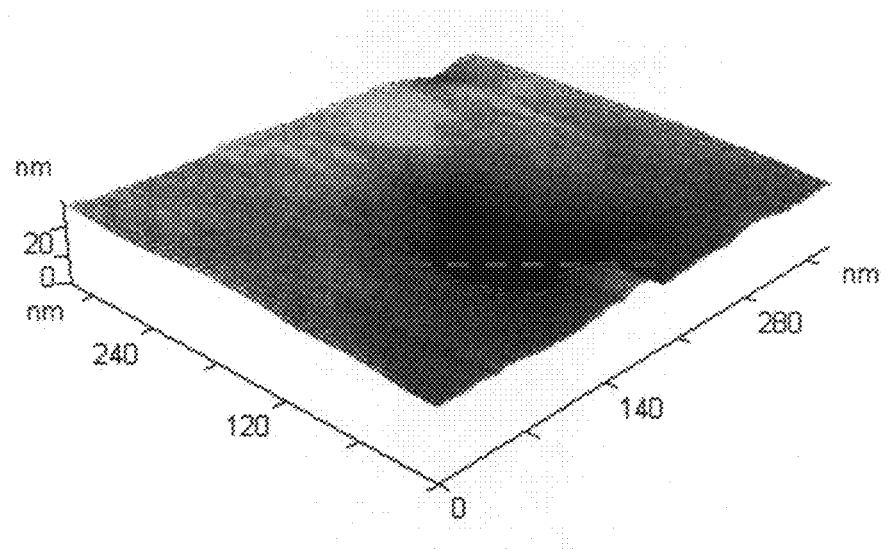
Figure 5F:
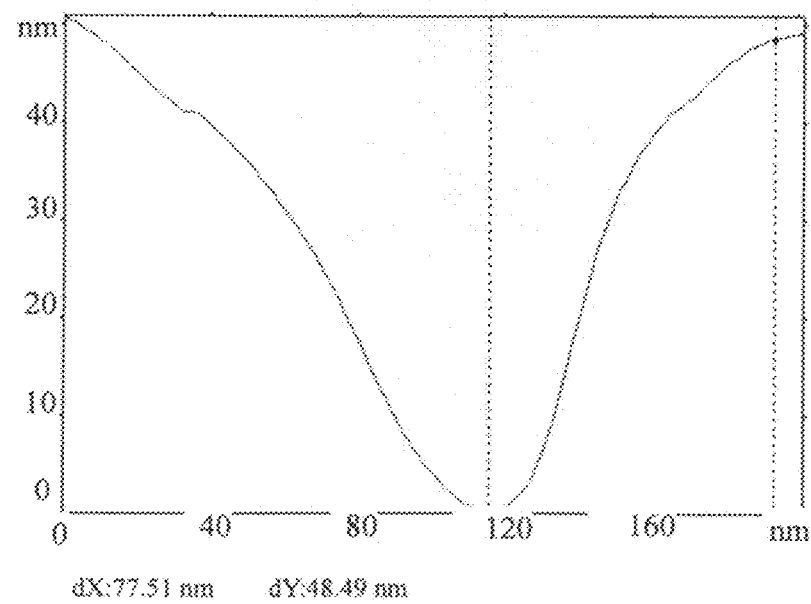

To study the effects of NP interactions on cell surface topology, imaging was performed on cells supplemented with a suspension of NPs at low concentration (80 µg/ml), serving to not saturate the cellular uptake of NPs (~500 µg/ml). Time-lapse images showed the eventual disappearance of NPs from cell surfaces when cells were incubated with modified NPs for 20 min, whereas cell surfaces remained covered with NPs when the same experiment was carried out with unmodified NPs (FIG. 3a-j). These results indicated more rapid cellular internalization of modified NPs than unmodified NPs. We also noticed that the cells incubated with modified NPs showed wrinkles on the cell surface following their internalization (FIG. 3(b) vs. 3(j)). All the time-lapse images (in height mode) were processed and analyzed using Femtoscan software. Cross sections of the images were generated along 10 different transects across the image (FIG. 4a-b), and the cross-sectional view was used to determine the elevations of NPs positioned on the cell surface. The average height of NPs at any time point was calculated from the mean of heights of 5-6 NPs on each of these 10 lines (FIG. 4c-d). The average height of unmodified NPs on the cell surface was determined to be 22 nm, compared to only 12 nm for the modified NPs on cell surface (5 min post-incubation with NPs; FIG. 4e). After an initial increase at 5 min, the height of unmodified NPs on cell surface did not change significantly, whereas that of the modified NPs continued to decrease (FIG. 4e). A similar trend was observed with the average surface roughness of the cells determined using the Femtoscan software. The cells incubated with unmodified NPs showed greater cell surface roughness than those incubated with modified NPs (FIG. 4f). Further, the surface roughness of the cells incubated with unmodified NPs decreased slowly after an initial increase at 5 min post incubation with NPs whereas that of the cells incubated with modified NPs decreased more rapidly and eventually reached the surface roughness of control cells (cells which were not incubated with NPs). The results thus demonstrate the rapid disappearance of modified NPs from the cell surface due to their cellular internalization whereas the slow decrease in surface roughness of the cells incubated with unmodified NPs suggest their relatively slow cellular internalization, and persistent presence on the cell surface (FIG. 3). Although clearly visible, the height and surface analysis data also suggest that the wrinkles seen on the surface of the cells incubated with modified NPs are insignificant in magnitude as these values are close to that for normal cells (in the absence of NPs). The images of the cell surface taken at different time points following incubation of NPs capture the process of NP internalization (FIG. 5a, b, c, d) and show formation of a typical endocytic pit on the cell surface, which "healed" to generate a normal-looking cell surface (FIG. 5e-f). The overall observations thus clearly demonstrate a distinctly different dynamic pattern of interactions of modified NPs with the cell membrane than that with unmodified NPs.

Coating of AFM Tip with NPs

Freshly cleaved mica surface was modified with NPs by allowing the preparation of NPs from their respective formulations on the mica surface. Preparation of NPs directly on the surface of freshly cleaved mica and imaging the same in air using AFM in tapping mode was performed as a feasibility experiment and helped to optimize the procedure for coating of the AFM probe tips (FIG. 6e). The image showed formation of NPs on mica surface covering approximately 95% of the mica surface with NPs. This method allowed the formation of NPs directly on the probe tips, and thus the coating of AFM tips was successfully performed with NPs.

Force Measurements on Live Cell Surface with NP-Modified AFM Tips

Figure 7C:
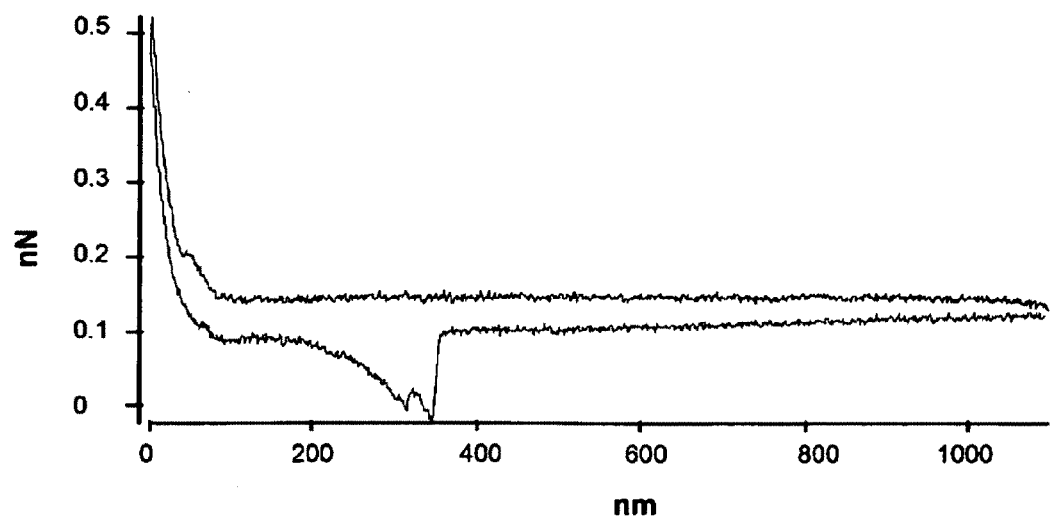
FIGS. 7c and 7d are typical/representative force curve for AFM tip modified with unmodified NPs and modified NPs, respectively.
Figure 7D:
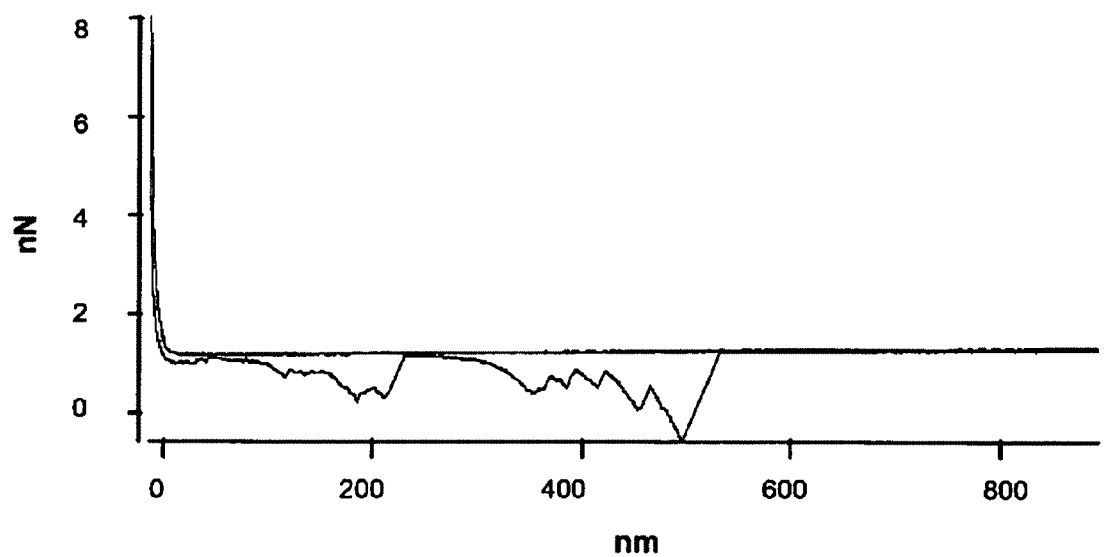
Figure 7E:
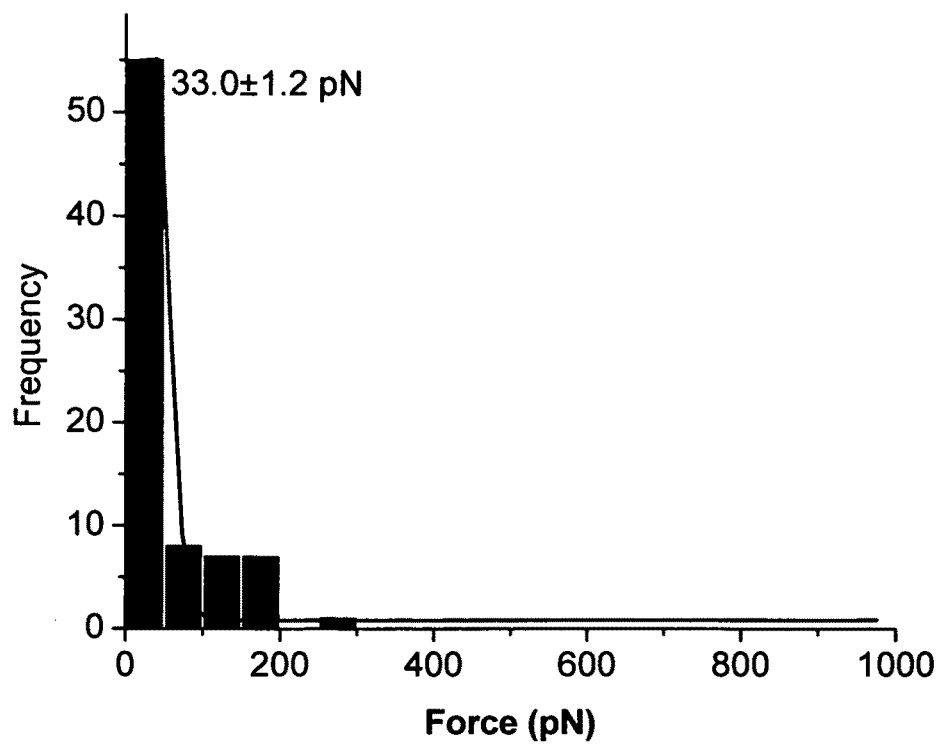
FIGS. 7e and 7f are graphical representations of the analysis of force distributions for unmodified NPs and modified NPs, respectively.
Figure 7F:
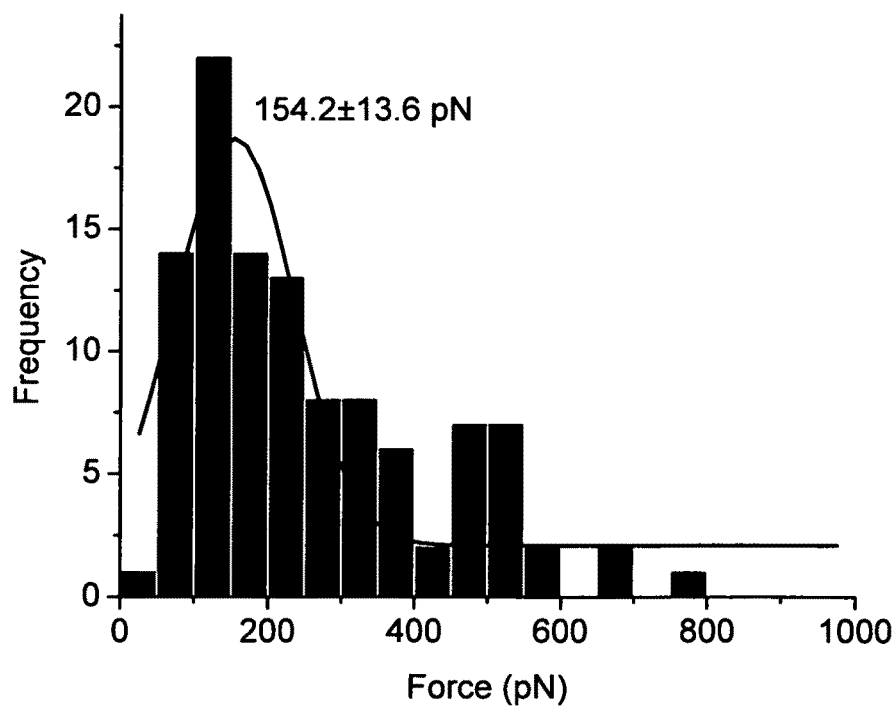
Figure 7G:
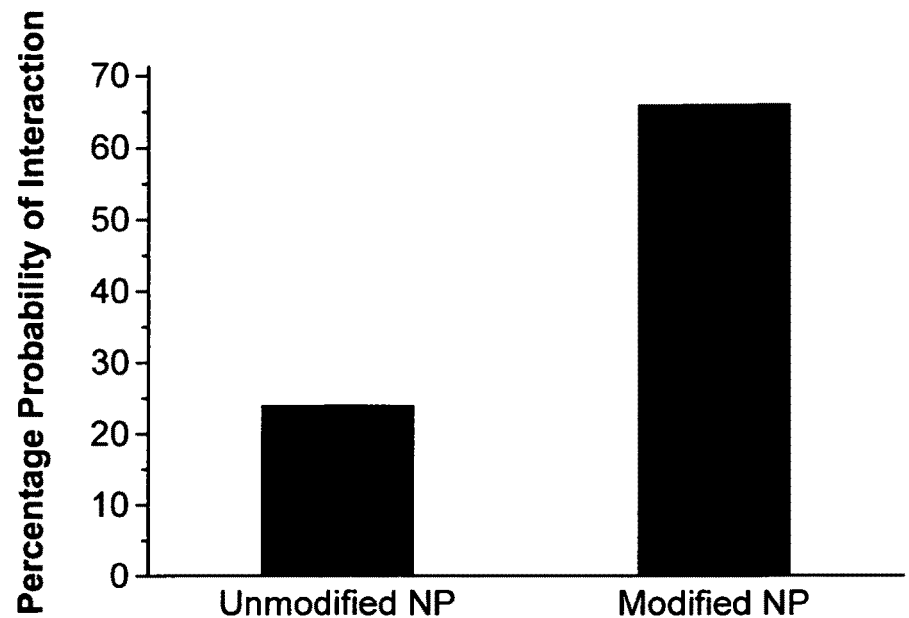
FIGS. 7g and 7h are graphs showing the probability of interaction of NP-coated tip and cell membrane, calculated as the percentage of force curves which show interactive forces of the total forces collected with the tip and the probability of occurrence of single and multiple force events was calculated for the unmodified and modified NPs, respectively.
Figure 7H:
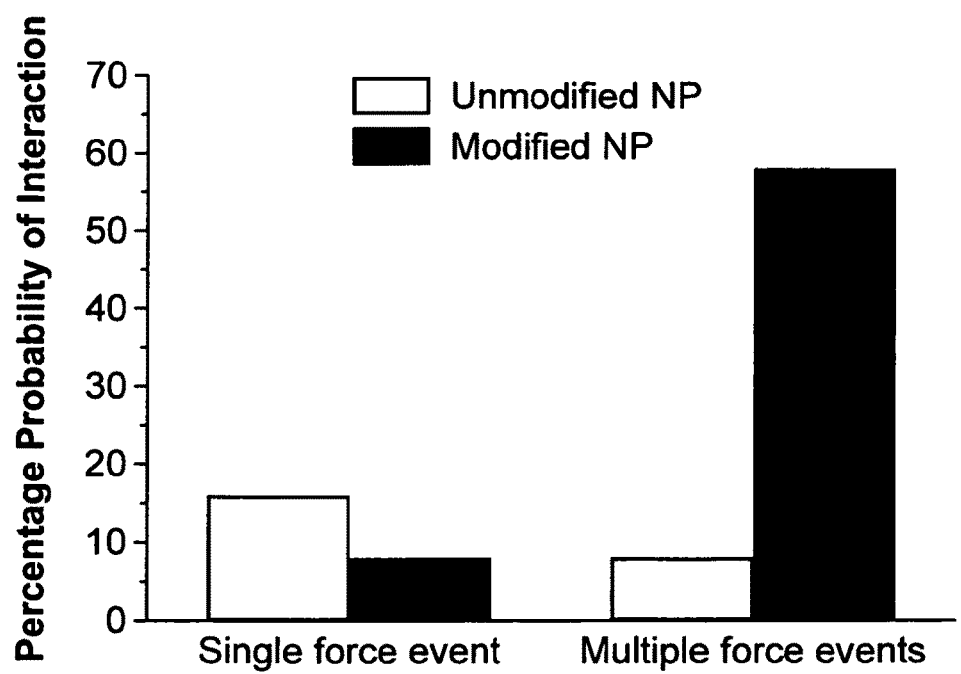

Typical force-distance curve obtained using the experimental setup for studying the NP-cell interactions is shown in FIG. 7 (FIG. 7c-d). Quantification of the force of interaction demonstrated remarkable differences in the relative affinities of the two formulations of NPs with cell surface (FIG. 7e-f). Modified NPs demonstrate higher affinity (5-fold) towards cell membranes, and interact more favorably showing multiple interactions with high force (154 pN); while the unmodified NPs show less interactions (33 pN) (FIGS. 7e and f). Probability of interaction of NP-modified tip and cell surface was calculated as the percentage of force curves which show interactive/adhesion forces of the total (n=500) forces collected with the tip. Modified NPs interact more favorably with cell membranes showing multiple interactions with components of cell membranes; while the unmodified NPs show fewer interactions (FIGS. 7g and h). The values of adhesion forces observed for both unmodified and surface-modified NPs were significantly above the noise level of the AFM instrument (~5 pN). The adhesion force measured with unmodified NPs was 280 pN (maximum) and 20 pN (minimum); whereas with modified NPs-1200 pN (maximum force) and a minimum force of 50 pN was recorded.

Cellular Uptake of NPs

NPs were prepared with different amounts of PVA and PLL to be used in the formulation of NPs. Uptake of NPs into cells was used as one of the responses to optimize the NP surface modification with PLL. NPs prepared with different amounts of PLL demonstrated significantly higher cellular uptake than unmodified NPs, however, no significant increase in uptake was observed for increasing PLL concentrations beyond 0.5% w/v in the NP formulations (FIG. 8a). This may be due to the increased size of NPs prepared with higher concentrations of PLL and lower concentration of PVA. The cellular uptake of NPs depends on the particle size; NPs with smaller size demonstrate greater internalization into cells [22]. Thus, this optimized formulation of NPs modified with PLL was selected for further studies and was termed as the modified NPs. The modified NPs demonstrated 2-3 fold higher cellular uptake, and greater intracellular retention in comparison to unmodified NPs (FIGS. 8a and b). The dose dependent studies indicated that the uptake of NPs increases with increasing dose of NPs, however the uptake of modified NPs was found to be higher than that of the unmodified NPs at all the doses (FIGS. 8c and d). The efficiency of NP uptake was reduced at higher doses for each kind of NPs, suggesting a saturable process of internalization (0.5% w/v), which showed similar size and zeta potential at pH=7 as unmodified NPs.

Exocytosis of NPs was also determined by evaluating the NP retention inside the cells using HPLC. There was no difference in the rate of exocytosis of modified and unmodified NPs. About 65% of the internalized NPs were exocytosed in the first 30 min after removal of the NPs from the medium. However, the modified NPs resulted in greater intracellular retention inside the cells when compared to the unmodified NPs (FIG. 8b).

Dynamics of Intracellular Trafficking

Figure 9:
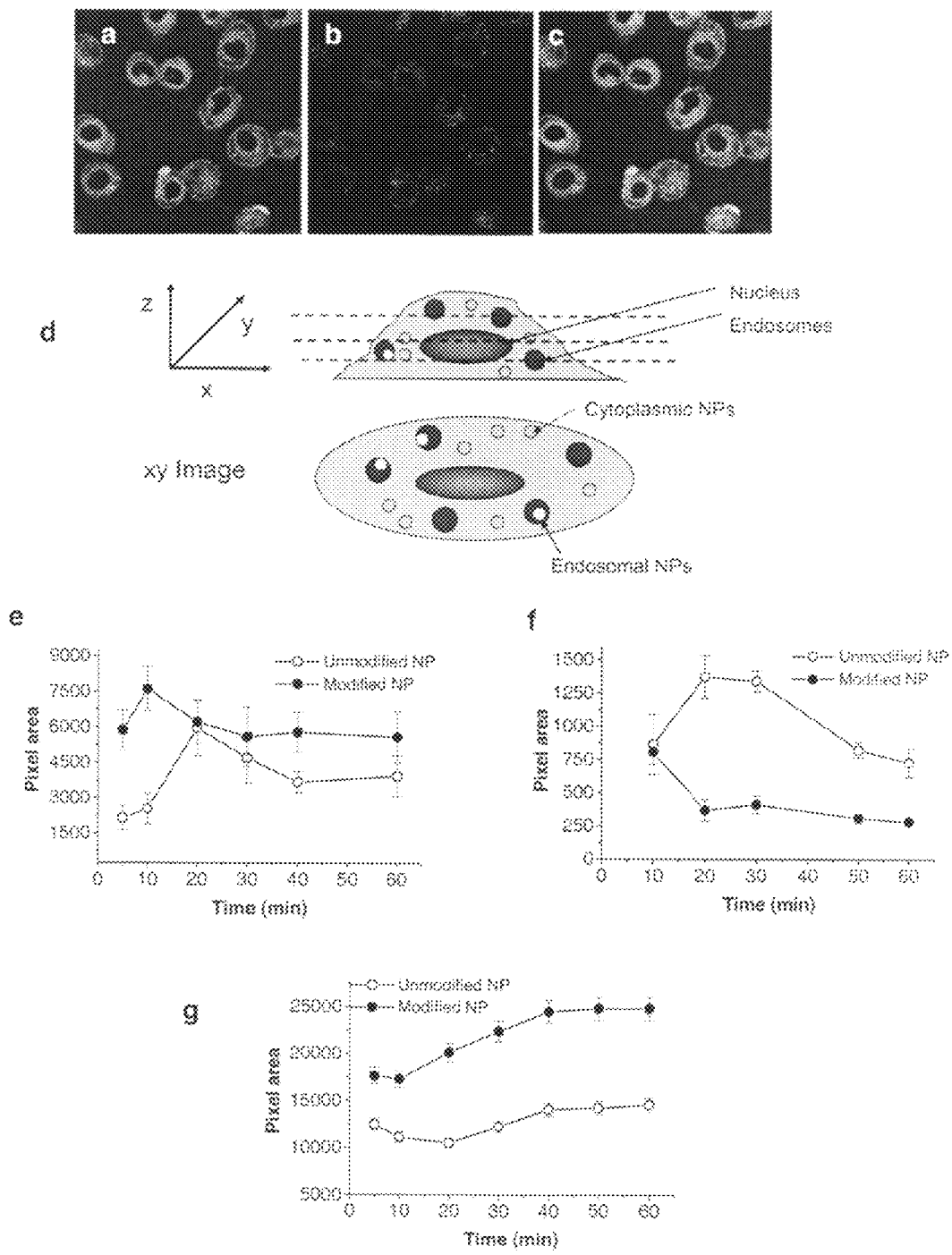
FIG. 9 illustrates the dynamics of subcellular sorting of NPs using quantitative 3-D analysis by confocal microscopy. Data is presented as mean±SEM, n=12. *Significant at p<0.05.

Confocal laser scanning microscopy was used for quantitative evaluation of the relative amounts of NPs localized in various subcellular compartments after endocytosis of NPs. Cells were incubated with fluorescently labeled (green) NPs (FIG. 9a) and Texas red labeled endosomal markers (FIG. 9b); co-localization of NPs in endosomes was observed (as yellow) from the overlap of green and red images (FIG. 9c). FIG. 9d shows a schematic illustrating the method used to quantify subcellular distribution of NPs. Results from these studies demonstrated a two- to three-fold greater cytoplasmic localization of modified NPs than unmodified NPs, suggesting the differences in dynamics of intracellular trafficking of the two formulations of NPs (FIG. 9). NP levels in EE increased through 10 and 20 min of incubation of cells with modified and unmodified NPs, respectively (FIG. 9e). This was followed by a decrease in NP levels in EE, as NPs progressed into LE. Levels of modified NPs in LE decreased sharply during first 20 min of incubation, whereas unmodified NPs demonstrated a slow gradual escape from LE after 30 min of incubation with NPs (FIG. 9f). Escape of NPs from LE was demonstrated by a decrease in the NP levels in LE, resulting in an increase in the NP levels in cytoplasm. Modified NPs demonstrated a relatively rapid and greater escape from the LE into the cytosolic compartment than unmodified NPs (FIG. 9g). Thus, selective modulation of NP surface charge (at acidic pH) from PLL-modification can govern the dynamics of subcellular sorting of NPs.

NP Uptake in Cells—Correlation with Force Measurements

The results suggested that the force of NP interaction with cell surface would determine their cellular uptake whereas the charge modulation determines the dynamics of their intracellular trafficking. The optimized formulation of surface-modified NPs demonstrated higher affinity towards cell membranes (by AFM studies) than unmodified NPs suggesting the differences in the cell-interactions of the two formulations. Further this can be very well correlated with the higher cellular uptake of modified NPs than that of unmodified NPs. Charge modulation on the surface of modified NPs facilitated their escape from endosomes into the cytosolic compartment of cells, and thus would allow a prolonged retention of NPs in the cell and potentially could allow sustained delivery of a therapeutic agent encapsulated in the NPs. Thus, HRP was used as a model protein to test the efficacy of NPs for intracellular delivery of proteins.

Sustained Intracellular HRP Levels with NPs

Figure 10:
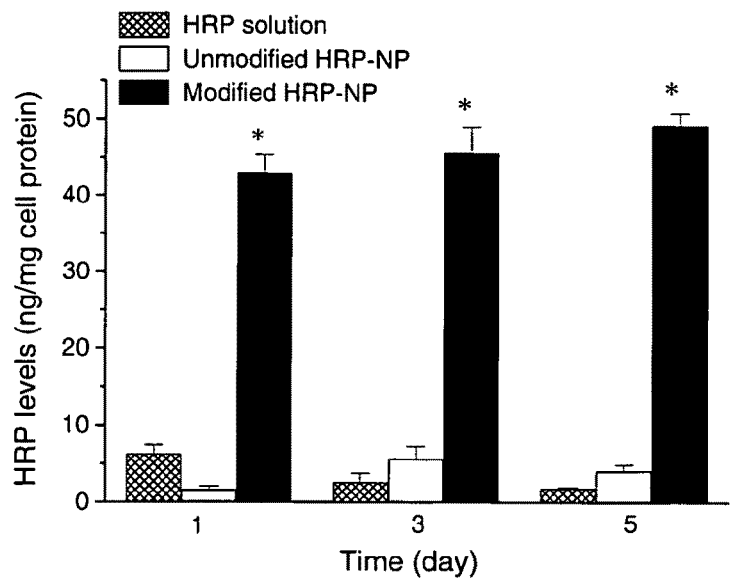
FIG. 10 is a graphical representation showing sustained cytoplasmic delivery of model enzyme-HRP in a time dependent manner (FIG. 10a) and in a dose dependent manner (FIG. 10b). Amount of active HRP was normalized to the total cell protein. Data is presented as mean±SEM, n=6. *Significant at p<0.005.
Figure 10:
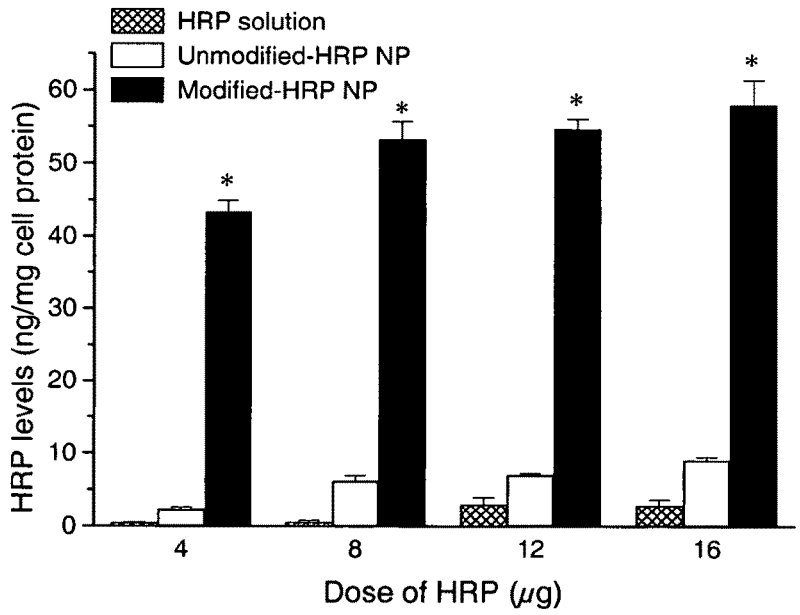

The greater cellular uptake and efficient endosomal escape of modified NPs resulted in significantly higher and sustained levels of activity (of a model enzyme—HRP) with HRP-loaded modified NPs, as compared to unmodified NPs. HRP loaded modified NPs demonstrated greater (5-6 fold) and sustained enzymatic activity of HRP as compared to the unmodified NPs and protein in solution (FIGS. 10a and b). Thus, greater cellular uptake of modified NPs resulted in significantly higher and sustained levels of activity (of a model enzyme—HRP) with HRP-loaded modified NPs, as compared to unmodified NPs. Also, dose-dependent HRP activity was obtained when cells were incubated with increasing doses of NPs.

The successful intracellular delivery of BSA and HRP as model proteins using the surface-modified NP composition described herein indicates that other macromolecular proteins, as well as small molecules having therapeutic activity can be delivered in a similar manner.

Certain patent and non-patent publications are cited throughout the foregoing specification in order to describe the state of the art to which this invention pertains. The entire disclosure of each of these citations is incorporated by reference herein.

While various embodiments of the present invention have been described and/or exemplified above, numerous other embodiments will be apparent to those skilled in the art upon review of the foregoing disclosure. The present invention is, therefore, not limited to the particle embodiments described and/or exemplified, but is capable of considerable variation and modification without departure from the scope of the appended claims.

PATENT REFERENCES

1. WO 98/56348—Kabanov et al.

NON-PATENT REFERENCES

1. Davda, J. and Labhasetwar, V., J. Biomed. Nanotechnology 1 (2005) 74-82.
2. Reddy, M. and Labhasetwar, V., International Stroke Conference, 2007, San Francisco, Calif.
3. Prabha, S. and Labhasetwar, V., Pharm. Res., 21 (2004), 354-64.
4. Song, C. et al., J. Control. Release, 54 (1998) 201-211.
5. Labhasetwar, V. et al., J. Pharm. Sci., 87 (1998) 1229-34.
6. Panyam, J. et al., Faseb J 16 (2002) 1217-26.
7. Sahoo, S., et al., J Control Release 82 (2002) 105-14.
8. Panyam, J. and Labhasetwar, V., Pharm Res., 20 (2003) 212-20.
9. Shlyaktenko, L. et al., Ultramicroscopy, 97 (2003) 279-287.
10. Schneider, S. et al., Proc. Natl. Acad. Sci. USA, 94 (1997) 316-321.
11. Ohnesorge, F. et al., Biophys. J., 73 (1997) 2183-2194.
12. Cho, S. et al., Cell Biol. Int., 26 (2002) 29-33.
13. Marchant, R. et al., Curr. Protein Pept. Sci., 3 (2002) 249-274.
14. You, H. and Yu, L., Methods Cell Sci., 21 (1999) 1-17.
15. McNally, H. et al., J. Neurosci. Methods, 142 (2005) 177-184.
16. Sinniah, K. et al., Curr. Eye Res., 25 (2002) 61-68.
17. Putman, C. et al., Biophys. J., 67 (1994) 1749-1753.
18. Schaus, S. and Henderson E., Biophys. J., 73 (1997) 1205-1214.
19. Pyo, N. et al., Colloids Surf B. Biointerfaces, 53 (2006) 278-287.
20. Davda, J. and Labhasetwar, V., Int. J. Pharm., 233 (2002) 51-59.
21. Panyam, J. et al., Int. J. Pharm., 262 (2003) 1-11.
22. Desai, M. et al., Pharm. Res., 14 (1997) 1568-73.
23. Mayer, B. and Hemmens, B., Trends Biochem. Sci. 22 (1997) 477-81.
24. Sarkar, R. and Webb, R., J. Vasc. Res., 35 (1998) 135-42.
25. Radomski, M. et al., Proc. Natl. Acad. Sci. USA, 87 (1990) 5193-7.
26. Zimmerman, G. et al., J. Clin. Invest., 98 (1996) 1699-1702.
27. Rome, J. et al., Arterioscler. Thromb., 14 (1994) 148-61.

The invention claimed is:

1. A surface modified nanoparticle for delivery of therapeutic agents, said surface modified nanoparticle comprising (i) a biocompatible polymer (ii) an amphiphilic emulsifier and (iii) a charge modulator, wherein said biocompatible polymer is poly(lactide-co-glycolide), said amphiphilic emulsifier is polyvinyl alcohol and said charge modulator is poly-L-lysine, (i), (ii) and (iii) forming a nanoparticle matrix, the weight ratio of said amphiphilic emulsifier to said charge modulator from which said nanoparticle is prepared is in the range of 4:1 to 1.5:1, said nanoparticle having a negative surface charge at neutral pH, said charge modulator being embedded in said nanoparticle matrix and extending from the nanoparticle surface, and said charge modulator being effective to reverse said surface charge from negative to positive in an acidic environment, thereby improving the efficiency of intracellular delivery of therapeutic agents carried by said nanoparticle, said surface modified nanoparticle having a greater force of adhesion to a cell membrane for enhancing cellular uptake of said nanoparticle as compared to an unmodified nanoparticle comprising said biocompatible polymer and said amphiphilic emulsifier without said charge modulator.

2. The modified nanoparticle of claim 1, further including a therapeutic agent.

3. A pharmaceutical preparation comprising a multiplicity of the nanoparticles of claim 2.

4. The modified nanoparticle of claim 1, further including a diagnostic agent.

5. A method for delivery of a therapeutic or diagnostic agent to a patient, said method comprising administering to said patient a multiplicity of nanoparticles as claimed in claim 1 also including an effective amount of said therapeutic or diagnostic agent.

* * * * *

UNITED STATES PATENT AND TRADEMARK OFFICE
CERTIFICATE OF CORRECTION

PATENT NO. : 8,865,216 B2  
APPLICATION NO. : 12/184715  
DATED : October 21, 2014  
INVENTOR(S) : Vinod Labhasetwar and Jaspreet Vasir Page 1 of 1

It is certified that error appears in the above-identified patent and that said Letters Patent is hereby corrected as shown below:

On the Title Page

Item (73), Assignees:
Please delete "National Institutes of Health (NIH), Bethesda, MD (US); U.S. Dept. of Health and Human Services (DHHS), Washington, DC (US)" and insert therefor --Board of Regents of the University of Nebraska, Lincoln, NE (US)--.

Signed and Sealed this  
Fourteenth Day of April, 2020

Andrei Iancu  
*Director of the United States Patent and Trademark Office*